US012629398B2

(12) United States Patent
Dandekar et al.

(10) Patent No.: US 12,629,398 B2
(45) Date of Patent: May 19, 2026

(54) METHOD OF ALLEVIATING OBSESSIVE COMPULSIVE DISORDER SYMPTOMS BY USE OF A MULTI-STRAIN PROBIOTIC FORMULATION

(71) Applicant: Unique Biotech Limited, Hyderabad (IN)

(72) Inventors: Manoj Pandurang Dandekar, Hyderabad (IN); Shubham Gopal Ghuge, Hyderabad (IN); Ziaur Rahman, Hyderabad (IN); Ratna Sudha Madempudi, Hyderabad (IN)

(73) Assignee: Unique Biotech Limited, Hyderabad (IN)

( * ) Notice: Subject to any disclaimer, the term of this patent is extended or adjusted under 35 U.S.C. 154(b) by 162 days.

(21) Appl. No.: 18/427,867

(22) Filed: Jan. 31, 2024

(65) Prior Publication Data

US 2024/0316128 A1    Sep. 26, 2024

(51) Int. Cl.
| | |
|---|---|
| *A61K 35/747* | (2015.01) |
| *A61K 31/198* | (2006.01) |
| *A61K 35/742* | (2015.01) |
| *A61K 35/745* | (2015.01) |
| *A61P 25/00* | (2006.01) |

(52) U.S. Cl.
CPC .......... *A61K 35/747* (2013.01); *A61K 31/198* (2013.01); *A61K 35/742* (2013.01); *A61K 35/745* (2013.01); *A61P 25/00* (2018.01)

(58) Field of Classification Search
CPC .. A61K 35/747; A61K 31/198; A61K 35/742; A61K 35/745; A61P 25/00
See application file for complete search history.

(56) References Cited

PUBLICATIONS

Dolan KE, Finley HJ, Burns CM, Gasta MG, Gossard CM, Parker EC, Pizano JM, Williamson CB, Lipski EA. Probiotics and Disease: A Comprehensive Summary—Part 1, Mental and Neurological Health. Integr Med (Encinitas). Oct. 2016;15(5):46-58. PMID: 27980495; PMCID: PMC5145013. (Year: 2016).*

* cited by examiner

*Primary Examiner* — Kade Ariani
(74) *Attorney, Agent, or Firm* — Jose Cherson Weissbrot

(57)    ABSTRACT

A method of treating, preventing or ameliorating at least one symptom of obsessive compulsive disorder (OCD) in a subject is disclosed. The method comprises a step in which a multistrain probiotic formulation is administered to the subject. The multistrain probiotic formulation includes the bacterial strains *Bacillus coagulans, Lactobacillus rhamnosus, Bifidobacterium lactis, Lactobacillus plantarum, Bifidobacterium breve* and *Bifidobacterium infantis* and Glutamine in a concentration range of 100-500 mg.

17 Claims, 10 Drawing Sheets

Specification includes a Sequence Listing.

H&E staining     alcian-blue PAS staining

METHOD OF ALLEVIATING OBSESSIVE COMPULSIVE DISORDER SYMPTOMS BY USE OF A MULTI-STRAIN PROBIOTIC FORMULATION

REFERENCE TO SEQUENCE LISTING

The substitute sequence listing is submitted as an ASCII formatted text filed via EFS-Web, with a file name of "Substitute_Sequence_Listing. TXT", a creation date of Jan. 25, 2024, and a size of 8,192 bytes. The substitute sequence Listing filed via EFS-Web is a part of the specification and is incorporated in its entirety by reference herein.

FIELD OF INVENTION

The current invention relates to the field of probiotic formulation for alleviating symptoms of obsessive-compulsive disorder (OCD). The current invention more specifically relates to method of preventing, ameliorating and treating OCD symptoms by using a multi-strain probiotic formulation.

BACKGROUND

Obsessive-compulsive disorder (OCD) is a complex neuropsychiatric condition affecting 2-3% of the population worldwide. OCD is characterized by the presence of obsessions and/or compulsions. Obsessions are described as recurrent and persistent thoughts, urges, or images that are experienced as intrusive and unwanted, whereas compulsions are stated as repetitive behaviours or mental acts that an individual feels driven to perform in response to an obsession or according to rules that must be applied rigidly.

Several putative pathophysiological mechanisms have been proposed for OCD including
immune dysregulation, endocrine and neurotransmitter dysfunction; however, the underlying pathophysiology remains unclear. The human gut microbiome, the collection of microbes and their genetic material in the human gastrointestinal tract, has gained immense interest in the field of psychiatry. To date, gut microbial differences have been noted in several clinical psychiatric populations including autism spectrum disorders (ASD), major depressive disorder (MDD), bipolar disorder, attention deficit hyperactivity disorder, post-traumatic stress disorder, psychosis and pediatric autoimmune neuropsychiatric disorder associated with streptococcal infections (PANDAS)/pediatric acute-onset neuropsychiatric syndrome (PANS).

There are several studies that have reported association of OCD with the gut microbiome. Recent findings have reported that gut dysbiosis (i.e., imbalance in the microbial community) which may impact the integrity of the intestinal wall, increase the colonization of pathogenic bacteria, and also modulate the production of neurotransmitters, proinflammatory cytokines, neurotrophic factors, hormones, neuropeptides and tryptophan metabolism can have a large impact on psychological disorders.

A study by Kantak et al (Ref 1) has shown the effect of *Lactobacillus* probiotic on OCD-like behaviour in mice. An altered gut microbiome signature has also been noted in depressive patients (Ref 2, Zheng et al), indicating the imbalance between beneficial and harmful bacterial colonies in the intestine of the host. There is increasing amount of scientific evidence demonstrating that gut microbiota can greatly influence all aspects of physiology. Emerging evidence also suggests that gut microbiota can influence brain function and behaviour through the 'microbiota-gut-brain axis' (Ref 3, Jiang et al). Thus, the remodelling of commensal gut microbiota has the potential to become one of the treatment strategies to more effectively relieve OCD symptoms. The profile of the gut microbiome can be modified using the administration of prebiotics, probiotics, postbiotics, and fecal microbiota transplantation (FMT).

The current invention encompasses the therapeutic potential and use of a multi-strain bacterial probiotic formulation in the management of OCD. The multi-strain probiotic formulation disclosed herein contains a consortium of probiotic microbes, belonging to *Bacillus* sp., *Lactobacillus* sp. and *Bifidobacterium* sp. Specifically, the consortium is of probiotic *Bacillus coagulans* Unique IS-2, *Lactobacillus rhamnosus* UBLR-58, *Bifidobacterium lactis* UBBLa-70, *Lactobacillus plantarum* UBLP-40, *Bifidobacterium breve* UBBr-01 and *Bifidobacterium infantis* UBBI-01. All the microbes are non-pathogenic to humans and animals. The probiotic formulation also comprises a non-essential amino acid "Glutamine".

The current invention encompasses a method of treating, preventing and/or ameliorating symptoms associated with OCD, by treating subjects with a multi-strain probiotic formulation for at least six weeks, with an effective dose regimen. In one aspect, the formulation is administered for 8 weeks. The current invention encompasses the use of a probiotic formulation comprising six unique bacterial strains in managing symptoms of OCD.

SUMMARY

One embodiment of the current invention is a method of treating, preventing or ameliorating at least one symptom of obsessive-compulsive disorder (OCD) in a subject, the method comprising the step of administering to the subject an effective dosage regimen of a multistrain probiotic formulation comprising the bacterial strains *Bacillus coagulans, Lactobacillus rhamnosus, Bifidobacterium lactis, Lactobacillus plantarum, Bifidobacterium breve* and *Bifidobacterium infantis.*

In one embodiment, the multistrain probiotic formulation comprises the bacterial strains *Bacillus coagulans* Unique IS-2 (MTCC 5260), *Lactobacillus rhamnosus* UBLR-58 (MTCC 5402), *Bifidobacterium lactis* UBBLa-70 (MTCC 5400), *Lactobacillus plantarum* UBLP-40 (MTCC 5380), *Bifidobacterium breve* UBBr-01 (MTCC 25081) and *Bifidobacterium infantis* UBBI-01 (MTCC 25124).

In one embodiment, the multistrain probiotic formulation further comprises 100-500 mg of Glutamine. In one embodiment, the multistrain probiotic formulation further comprises 250 mg of Glutamine.

In one embodiment, method as disclosed herein, wherein the multistrain probiotic formulation comprises *Bacillus coagulans:Lactobacillus rhamnosus:Bifidobacterium lactis: Lactobacillus plantarum:Bifidobacterium breve* and *Bifidobacterium infantis* in the ratio 2:2:2:2:1:1.

In one embodiment, the bacterial strains are present in the multistrain probiotic formulation at $10^6$-$10^{12}$ colony forming unit (cfu) per dose. In one embodiment, the method as disclosed herein, wherein 1 to 2 doses of the multistrain probiotic formulation are administered to the subject per day. In one embodiment, the multistrain probiotic formulation is administered to the subject for at least 6 weeks. In one embodiment, the multistrain probiotic formulation is administered to the subject for 6-8 weeks.

In one embodiment, the method as disclosed herein, wherein an effective dosage regimen of the multistrain probiotic formulation comprises administering 1 to 2 doses per day of the multistrain probiotic formulation, for 6-8 weeks.

In one embodiment, the multistrain probiotic formulation is administered to the subject as an adjunct to standard OCD treatment. In one embodiment, the multistrain probiotic formulation is administered to the subject in the form of a food product, a dietary supplement or a pharmaceutically acceptable composition.

In one embodiment, the amelioration of OCD symptoms in the subject by administration of an effective dosage regimen of the multistrain probiotic formulation comprises a reduced level of repetitive behavior in the subject.

In one embodiment, the method as disclosed herein, wherein the multistrain probiotic formulation produces Gamma-aminobutyric acid (GABA) from glutamine in the subject. In one embodiment, the administration of an effective dosage regimen of the multistrain probiotic formulation leads to increase in levels of GABA in the subject. In one embodiment, the method as disclosed herein, wherein the amelioration of OCD symptoms is due to increase in Gamma-aminobutyric acid (GABA) levels in the subject.

In one embodiment, the administration of an effective dosage regimen of the multistrain probiotic formulation leads to a decrease in levels of nNOS in the subject.

In one embodiment, the administration of an effective dosage regimen of the multistrain probiotic formulation leads to a change in the gut microbiota in the subject.

In one embodiment, administration of an effective dosage regimen of the multi-strain probiotic formulation disclosed herein reverses the elevated mRNA expression levels of IL-6, TNF-α and C-reactive associated with OCD in the subject.

BRIEF DESCRIPTION OF FIGURES AND SEQUENCE LISTING

FIG. 1A is a graph depicting the effect of the multistrain probiotic formulation on anxiety-like behavior in EPM (elevated plus maze) test. The results are presented as % Time spent in the open arms=(Time spent in open arms/Total time spent in open and closed arms)×100.

FIG. 1B is a graph depicting the effect of the multistrain probiotic formulation on anxiety-like behavior in EPM (elevated plus maze) test. The results are presented as % Entries into open arms=(Number of entries in open arms/Total number of entries in open and closed arms)×100. Values are presented as mean±S.E.M. for 6-8 rats. $p<0.0003, ***p<0.0001; @ p<0.0011 vs. respective vehicle: *p<0.039, **p<0.009 and #p<0.0001 vs. respective quinpirole group.

FIGS. 2A, 2B, and 2C are graphs depicting the effect of multistrain probiotic on repetitive- and compulsive-like behavior in marble burying test. self-grooming test, and hole board test respectively. Values are plotted as mean±S.E.M. for 6-8 rats. *p<0.0001 vs. respective vehicle: p<0.0014, #p<0.0001, and @ p<0.0001 vs. respective quinpirole group.

FIG. 3 shows a graph depicting the locomotor activity in OFT. Values are plotted as mean±S.E.M. for 6-8 rats. No bar is significantly different from the quinpirole group.

FIG. 4A is a western blot analysis of nNOS in the frontal cortex of rat (n=3). In densitometric analysis, an increased expression of nNOS was seen in quinpirole-treated animals compared to the vehicle group. Multistrain probiotic and fluoxetine decreased the expression of nNOS vs. quinpirole.

Figure 6A:
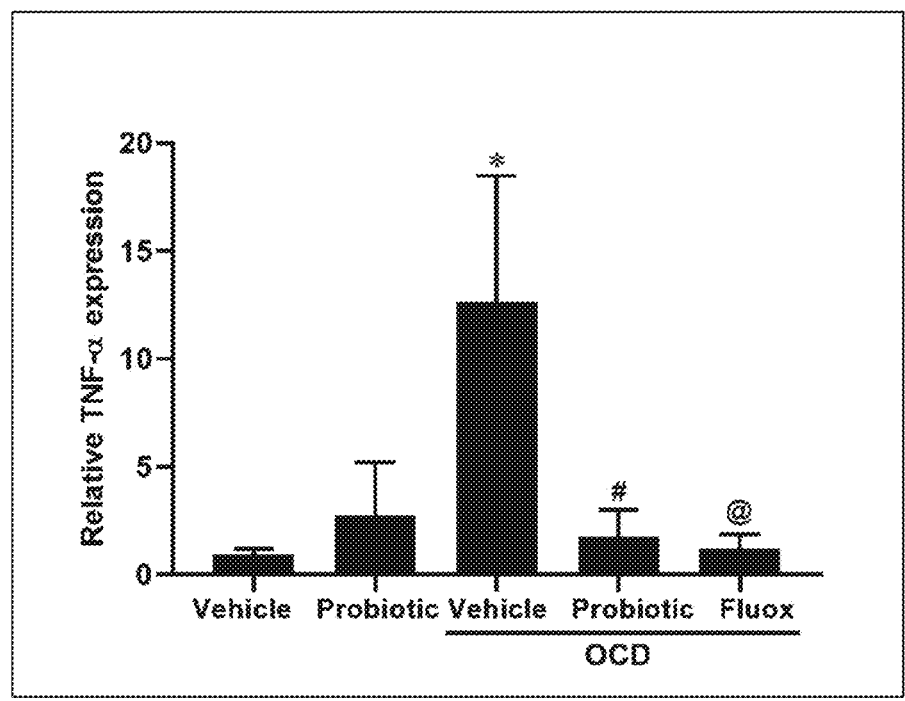
Figure 6B:
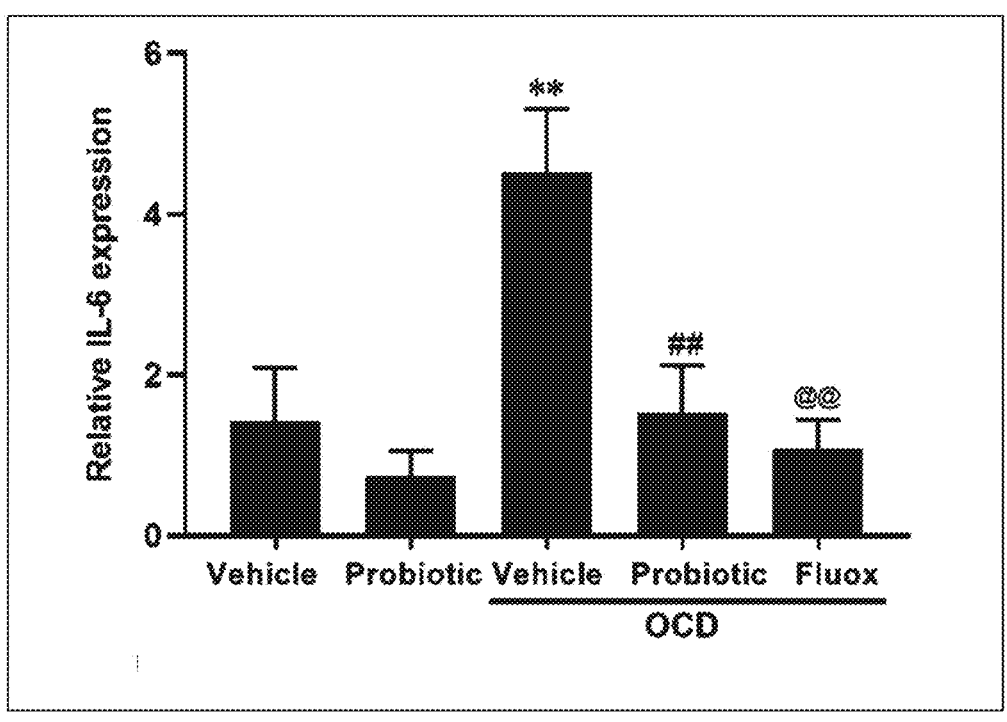
Figure 6C:
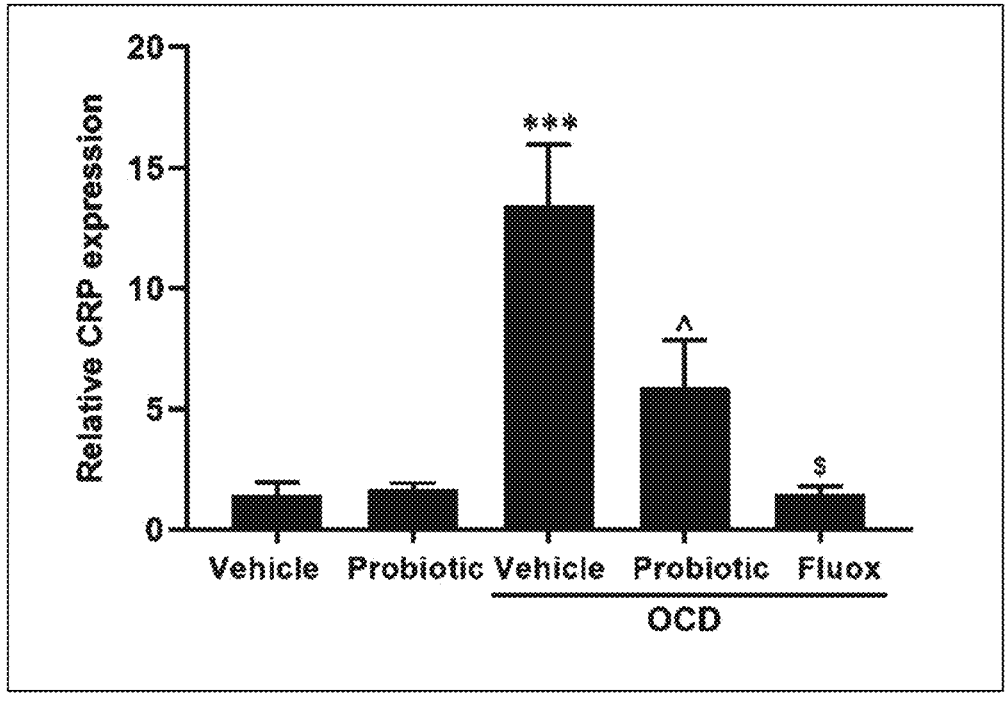

FIGS. 6A, 6B and 6C are Graphs showing real-time PCR results of inflammatory cytokines in the amygdala of rats (n=5-6). Multistrain probiotic and fluoxetine treatment prevents mRNA expression of (FIG. 6A) TNF-α, (FIG. 6B) IL-6, and (FIG. 6C) CRP compared to the quinpirole group. Values are plotted as mean±S.E.M. p<0.0162 and *p<0.0001 vs. vehicle: #p<0.0207, ^ p<0.0118, @ p<0.0267, **p<0.002, $ p<0.0001, @ p<0.0207 and @@ p<0.0118 vs. respective quinpirole group.

Figures 7A, 7B:
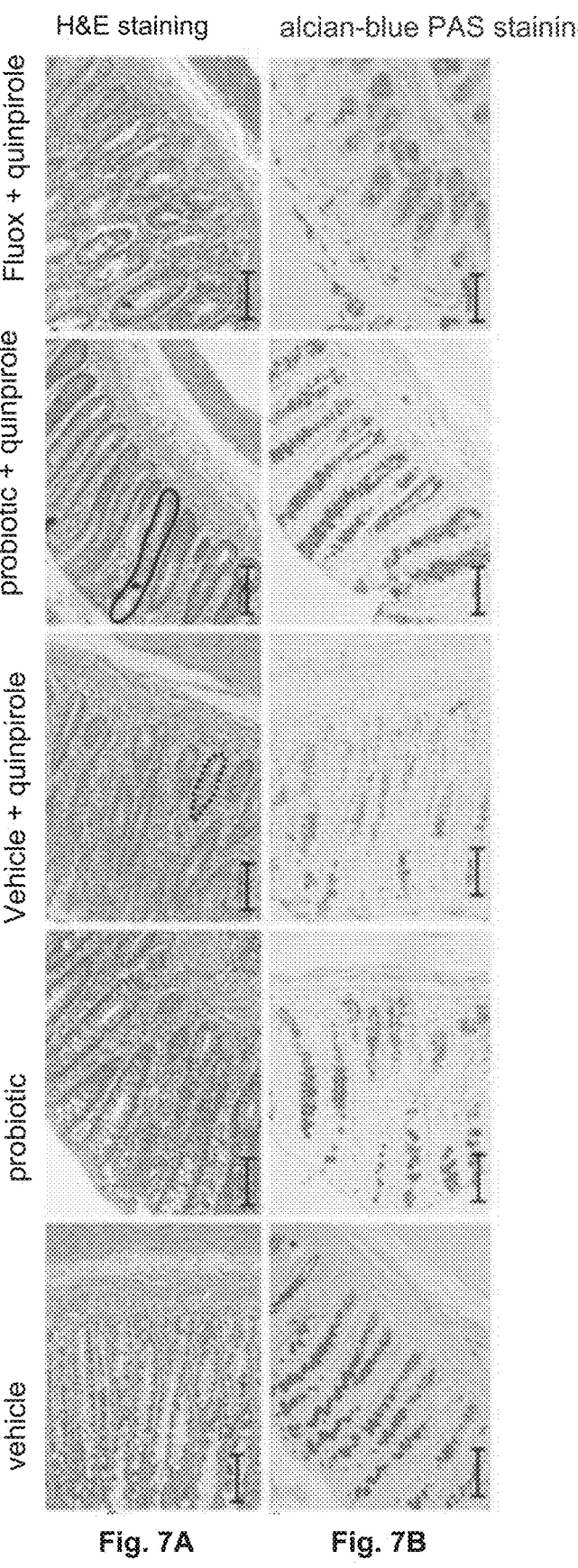

FIGS. 7A and 7B shows Photomicrographs depicting the hematoxylin and eosin staining and Alcian blue-PAS staining respectively. One of the crypts and villi is demarcated by dotted and solid lines, respectively.

Figure 7C:
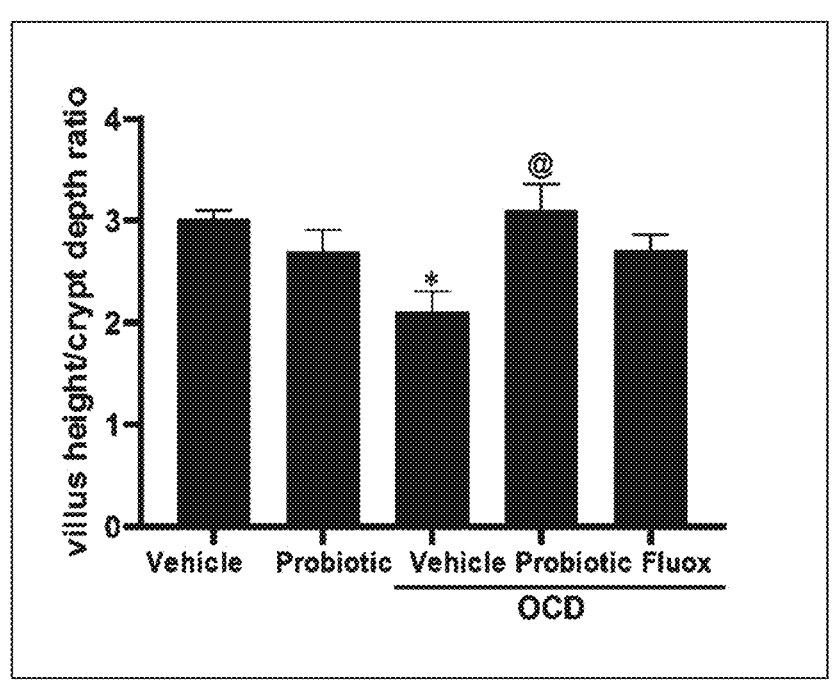

FIG. 7C shows bar graph depicting the villus-to-crypt length ratio, and

Figure 7D:
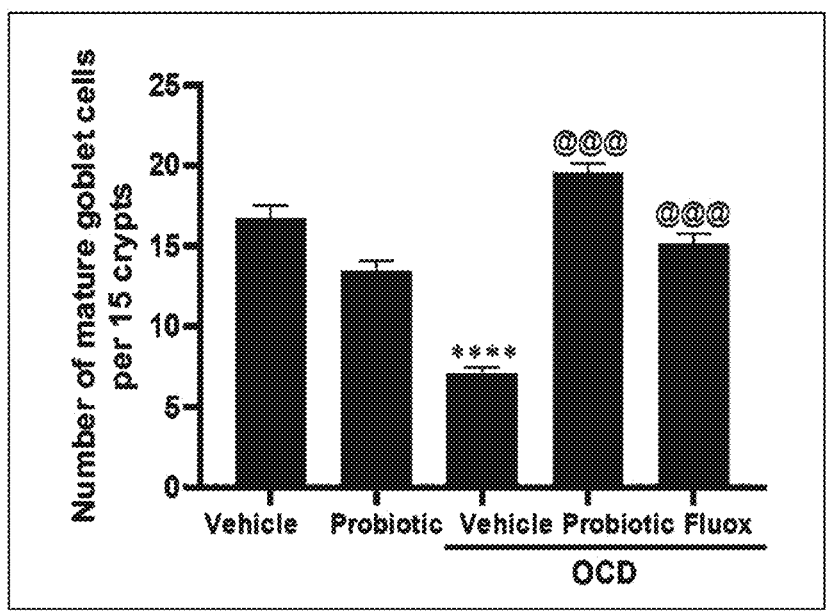

FIG. 7D shows the number of mature goblet cells. Values are plotted as mean±S.E.M. of 3-4 rats. *p<0.0394 and ***p<0.0001 vs. vehicle; #p<0.0266, @p<0.0366, ##p<0.0001 and @@p<0.0001 vs. respective quinpirole group.

Figure 8A:
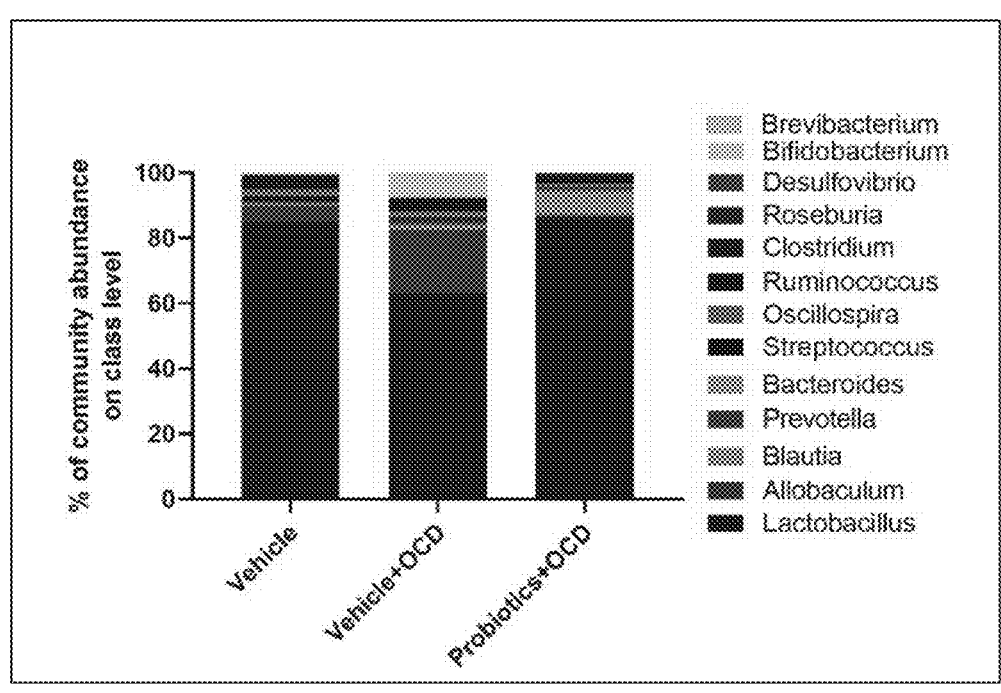

FIG. 8A. shows graphs representing 16S rRNA gene sequencing analysis of fecal samples (n=3). Bar graph in FIG. 8A depicts the relative abundance of microbiota at the class level across the vehicle, vehicle+OCD, and probiotic+OCD groups. Values are plotted as mean±S.E.M.

Figure 8B:
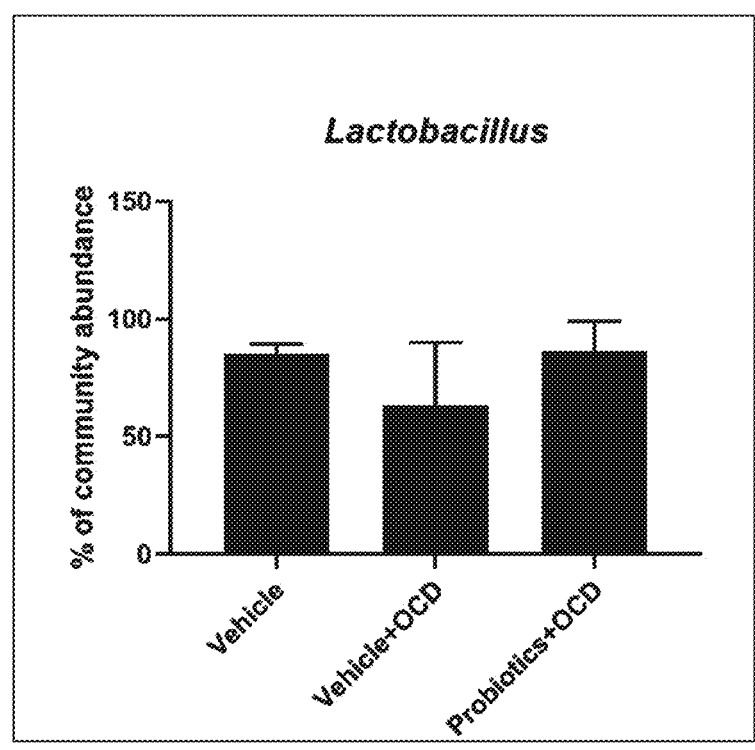

FIG. 8B shows graphs representing 16S rRNA gene sequencing analysis of fecal samples (n=3). The bar graph in FIG. 8B represents the percent community abundance of *Lactobacillus* across the vehicle, vehicle+quinpirole, and probiotic+quinpirole groups. Values are plotted as mean±S.E.M.

Figure 8C:
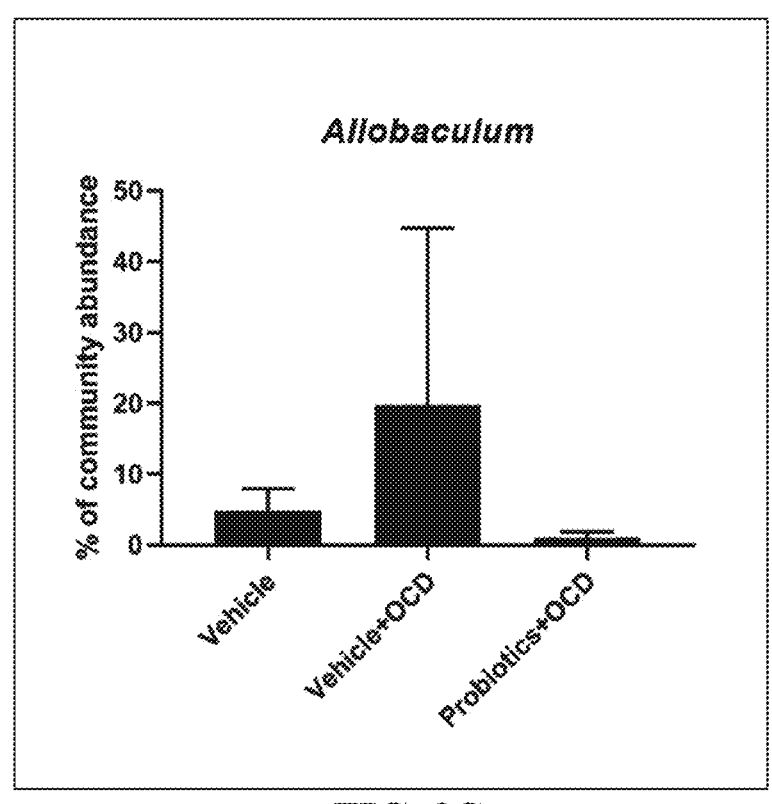

FIG. 8C shows graphs representing 16S rRNA gene sequencing analysis of fecal samples (n=3). The bar graph FIG. 8C represents the percent community abundance of *Allobaculum* across the vehicle, vehicle+quinpirole, and probiotic+quinpirole groups. Values are plotted as mean±S.E.M.

Figure 8D:
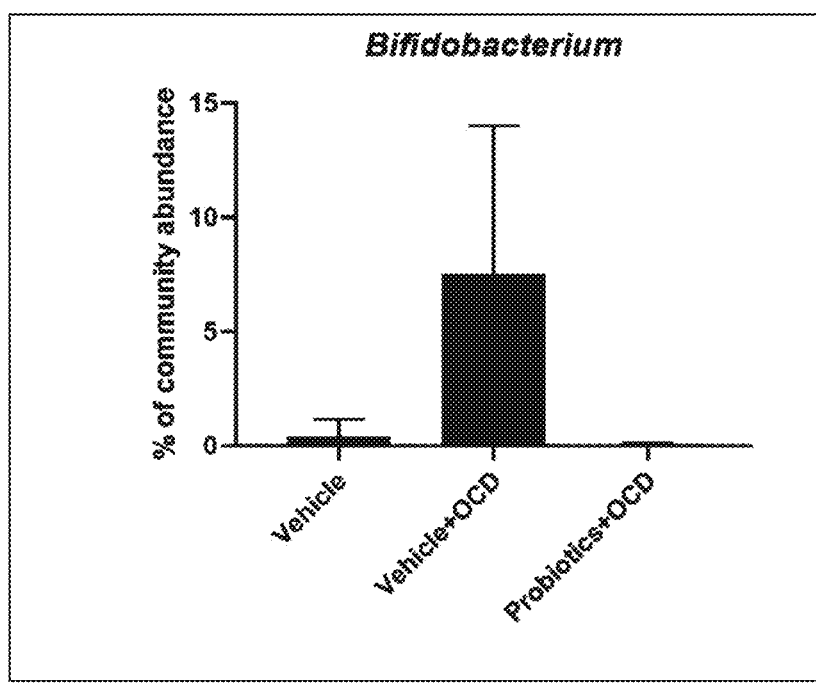

FIG. 8D shows graphs representing 16S rRNA gene sequencing analysis of fecal samples (n=3). The bar graph in FIG. 8D represents the percent community abundance of *Bifidobacterium* across the vehicle, vehicle+quinpirole, and probiotic+quinpirole groups. Values are plotted as mean±S.E.M.

DETAILED DESCRIPTION

Obsessive-compulsive disorder (OCD) is a complex neuropsychiatric condition affecting 2-3% of the population worldwide. OCD is characterized by the presence of obsessions and/or compulsions. Obsessions are described as recurrent and persistent thoughts, urges, or images that are experienced as intrusive and unwanted, whereas compulsions are stated as repetitive behaviours or mental acts that an individual feels driven to perform in response to an obsession or according to rules that must be applied rigidly.

Several putative pathophysiological mechanisms have been proposed including immune dysregulation, endocrine and neurotransmitter dysfunction; however, the underlying pathophysiology remains unclear.

The human gut microbiome, the collection of microbes and their genetic material in the human gastrointestinal tract, has gained immense interest in the field of psychiatry of late. To date, gut microbial differences have been noted in several clinical psychiatric populations including autism spectrum disorders (ASD), major depressive disorder (MDD), bipolar disorder, attention deficit hyperactivity disorder, post-traumatic stress disorder, psychosis and pediatric autoimmune neuropsychiatric disorder associated with streptococcal infections (PANDAS)/pediatric acute-onset neuropsychiatric syndrome (PANS).

Compulsions are usually defined by certain criteria, some of which are: 1. Repetitive behaviours (e.g., hand washing, ordering, checking) or mental acts (e.g., praying, counting, repeating words silently) that the person feels driven to perform in response to an obsession, or according to rules that must be applied rigidly; and the behaviours or mental acts are aimed at preventing or reducing distress or preventing some dreaded event or situation.

The current invention encompasses the therapeutic potential and use of a multi-strain bacterial probiotic formulation in the management of OCD.

The multi-strain probiotic formulation disclosed herein comprises the probiotic bacteria *Bacillus coagulans, Lactobacillus rhamnosus, Bifidobacterium lactis, Lactobacillus plantarum, Bifidobacterium breve* and *Bifidobacterium infantis*. All the microbes are non-pathogenic to humans and animals. The probiotic formulation also comprises a non-essential amino acid "Glutamine".

More specifically, the multi-strain probiotic formulation comprises the strains *Bacillus coagulans* Unique IS-2, *Lactobacillus rhamnosus* UBLR-58, *Bifidobacterium lactis* UBBLa-70, *Lactobacillus plantarum* UBLP-40, *Bifidobacterium breve* UBBr-01 and *Bifidobacterium infantis* UBBI-01 and Glutamine.

All the strains in this probiotic formulation were isolated and deposited in MTCC (Microbial type culture collection) and ATCC by Unique Biotech.

*Bifidobacterium* is a genus of gram-positive, anaerobic, and nonmotile bacteria. Similar to *Lactobacillus, Bifidobacterium* species are abundant occupants of the gastrointestinal tract. *Bacillus coagulans* is a spore-forming, lactic acid-producing, and facultative non-pathogenic anaerobic bacterium, which can survive in the extreme microenvironment of the intestine and germinate in the small intestine.

*Lactobacillus plantarum* is a gram-positive, nonmotile, non-spore-forming bacterium. *Lactobacillus plantarum* is a widely distributed lactic acid bacterium. It represents part of the microbiota of many foods and feeds, including dairy, meat, fish, vegetable fermented products (e.g., must, sauerkraut, pickled vegetables, sourdoughs), and silage: it is also a natural inhabitant of the human and animal mucosa (oral cavity, gastrointestinal tract, vagina, etc.) (Ref 4, Sulthana et al).

*Lactobacillus rhamnosus* is a gram-positive lactic acid bacterium that is part of the normal gut microflora in humans. *L. rhamnosus* is a gram-positive short heterofermentative anaerobe. Currently, clinical trials are being conducted on probiotic *L. rhamnosus* for dermatitis, diabetes mellitus, colorectal cancer, ulcerative colitis, Crohn's disease, constipation, diarrhoea irritable bowel diseases, candidiasis, rheumatoid arthritis, and polycystic ovary syndrome.

The probiotic strain, *Bacillus coagulans* Unique IS-2 (MTCC 5260, ATCC PTA-11748), has also been found to be efficacious in the treatment of diarrhoea, IBS, IBD, constipation, bacterial vaginosis, dental caries and hypercholesterolemia.

The probiotic formulation disclosed also contains a non-essential amino acid glutamine. Glutamine is given as a precursor to the microbes so that they can utilize the amino acid and produce a useful metabolite, such as gamma-aminobutyric acid (GABA). Glutamine is the precursor to the formation of GABA in the brain.

Definitions:

As used herein, "ameliorating, treating or preventing symptoms of obsessive-compulsive disorder (OCD)" includes, the amelioration or alleviation, at least in part, of one or more symptoms of OCD, such as repetitive or recurrent behaviours, urges, and thoughts.

Further, "treating or preventing" includes preventing the development of OCD in a subject or individual who may be predisposed to such a condition or may display one or more symptoms of such a condition but has not yet been diagnosed with the condition. "Treating or preventing" also includes preventing the onset of appearance of symptoms.

As used herein, the terms "composition" and "formulation" are used interchangeably.

As used herein, the term "patient" and "subject" refers to the person or individual suffering from, or showing the symptoms of OCD, or a patient who is predisposed to OCD.

As used herein "effective dosage regimen" refers to the specific way a therapeutic drug is to be taken, including formulation, route of administration, dose, dosing interval, and treatment duration, so as to have the desired effect.

In the current invention "effective dosage regimen" of the multistrain probiotic formulation has the desired effect of preventing, treating and/or ameliorating OCD symptoms.

As used herein, the term "dose" refers to the measured and specific amount of a therapeutic composition, administered at one time. The number, and frequency of doses given over a specified period of time or prescribed intervals makes up the dosage regimen.

The term "conventional pharmaceuticals or compounds" or "conventional OCD therapy" or "Standard Medical Treatment" as used herein in the context of "other conventional pharmaceuticals or compounds used to treat behavioral disorder/symptoms" and refers to those pharmaceuticals or compounds that persons of skill in the art (including but not limited to physicians) conventionally use to treat the "condition/disorder/symptom" or "behavioural abnormality" associated with OCD.

Conventional OCD treatment includes Serotonergic antidepressants, such as selective serotonin reuptake inhibitors (SSRIs) and clomipramine, which are the first-line treatment of OCD. In case of significant improvement with these treatments, maintenance treatment is necessary. Unfortunately, about half of the patients do not respond sufficiently to oral serotonergic antidepressants; and augmentation with atypical antipsychotics is an established second-line drug treatment strategy. Alternatives include intravenous serotonergic antidepressants and combination with or switch to cognitive behavioral psychotherapy (Ref 5, Kellner et al).

Moreover, patients with OCD show a considerably lower placebo response than subjects with other anxiety disorders, which is not caused by differential expectancy. This phenomenon, and data about the rarity of spontaneous remission of OCD in all age groups, make treatment with for the necessity of other effective therapeutic approaches also to try to reduce long-term morbidity. Preliminary evidence also supports the usefulness of cognitive-behavioral therapy (CBT) as a nonpharmacological augmentation treatment.

Glutamatergic agents, such as memantine, an N-methyl-Daspartate (NMDA) glutamate receptor antagonist, are among the most promising new candidates in the treatment of OCD. Adjunctive glycine (an NMDA glutamate receptor agonist) was also tested in a small double-blind placebo-controlled trial and approached efficacy for treatment of OCD symptoms. Glutamate-modulating agent riluzole, amantadine which is also an NMDA antagonist) are also promising OCD drugs.

About 40-60% of OCD sufferers do not respond to appropriate courses of treatment with serotonin reuptake inhibitors (SRI) and even to combination of medicines. Those OCD patients who do not achieve a satisfactory response after an adequate trial of first-line therapies are described as treatment-resistant. The satisfactory response is usually defined by a reduction in the Yale-Brown Obsessive Compulsive scale score ≥35% or ≥25% with respect to baseline [Ref 6, Margoob et al].

The term "treatment-resistant OCD" or "refractory OCD" as used herein refers to any form of OCD that in any one or more given individuals has not responded to at least one adequate trial with anti-obsession therapy, or that responds to a lesser extent or displays a diminished or reduced response to said treatment when compared to OCD in a subject who displays no resistance to said treatment. Thus, "treatment-resistant OCD" may indicate complete or partial resistance to treatment.

The term "prevention" as used herein indicates any activity that reduces the burden of the individual later expressing those behavioural symptoms. This takes place at primary, secondary and tertiary prevention levels, wherein: a) primary prevention avoids the development of symptoms/disorder/condition: b) secondary prevention activities are aimed at early stages of the condition/disorder/symptom treatment, thereby increasing opportunities for interventions to prevent progression of the condition/disorder/symptom and emergence of symptoms; and c) tertiary prevention reduces the negative impact of an already established condition/disorder/symptom by restoring function and reducing any condition/disorder/symptom or related complications.

Pharmaceutical preparations comprising the multistrain probiotic formulations disclosed herein may be in the form of solids such as tablets, granules, powders, capsules, and liquids such as solutions, emulsions, suspension and the like.

Pharmaceutically acceptable or appropriate carriers for use in the pharmaceutical preparations comprising the multistrain probiotic formulations disclosed herein can be, but are not limited to, organic or inorganic, solid or liquid excipients which is suitable for the selected mode of application such as oral application or injection, and administered in the form of a conventional pharmaceutical preparation. Examples of carriers or excipients in the preparation include, but are not limited to starch, lactose, glucose, sucrose, dextrin, cellulose, paraffin, fatty acid glyceride, water, alcohol, gum arabic and the like. If necessary, auxiliary, stabilizer, emulsifier, lubricant, binder, pH adjustor controller, isotonic agent and other conventional additives may be added.

Neurotransmitters:

Neurotransmitters (NTs), are endogenous chemical messengers that carry and amplify nerve-to-nerve signaling or signals between nerves and other cell types; and play an essential role in information transmission throughout the CNS and peripheral nervous system. NTs crucial for communicating sensory, motor, and integrative neuronal messages, affecting many functions, such as emotions, thoughts, memories, movements, and sleep patterns. Abnormal levels of NTs are reflected in dysregulation of brain functions, leading to physical, psychotic, and neurodegenerative diseases. Glutamate is one of the dominant excitatory NT in the CNS, it can be produced from glutamine and is the precursor of GABA, as well as for the amino acid glutamine and the antioxidant molecule glutathione (Ref 7, Hadi et al).

Interestingly, glutaminergic agents, all work by different, and in some cases opposite, mechanisms in OCD patients, hence studying and elucidating the role of glutamate dysregulation in the etiology of OCD, and of glutamate modulators in its treatment is important in finding new therapies for OCD.

GABA is the main inhibitory NT in the brain and is formed through glutamate decarboxylase (EC 4.1.1.15) conversion of glutamate to GABA or is produced by commensal microorganisms from gut microbiota. Thus, it is widely accepted that low levels of GABA are responsible for the hyperexcitability of neurons.

The glutamine-glutamate cycle in the nervous system is well known. Astrocytes and neurons are connected by a flow of glutamine (produced directly from glutamate) from astrocytes to neurons. In the neurons glutamine is converted to transmitter glutamate and GABA. However, after their release as transmitters most of the glutamate and a considerable amount of GABA are returned to astrocytes. This is the glutamine-glutamate (GABA) cycle (Ref 8, Hertz). Changes in GABAergic neurotransmission is associated with numerous CNS disorders, such as behavioral disorders, pain, and sleep, stress and depression. Impaired GABA homeostasis has been linked to several neurological disorders (e.g., autism spectrum disorders, schizophrenia, epilepsy and neurodegenerative diseases) GABA level imbalance has also been correlated to OCD (Ref 9, Biria et al).

Nitric oxide (NO) is one of the important neurotransmitters, which is known to influence behaviours like learning, pain perception, aggression, depression and anxiety. There is a lot of evidence suggesting the role of NOS in OCD. SSRIs that are commonly used as anti-compulsive agents, are reported to inhibit nitric oxide synthase (NOS) activity, and lead to reduction in the interferon-gamma-induced production of nitric oxide in microglia. The nNOS (neuronal nitric oxide synthase) is also reported to co-localize with dopaminergic neurons, where they have regulatory role over each other. Moreover, glutamate which an excitatory neurotransmitter, is reported to activate nNOS via Ca2+/calmodulin complex, indicating the role of NO in OCD. OCD patients have also been reported to have higher plasma nitrate levels. These evidences point towards the role of NO in obsessive-compulsive behaviour as well as in the anti-compulsive effect of therapeutically used drugs.

Serotonin biosynthesis constitutes another humoral gut-brain communication pathway that might be affected by SCFAs (short chain fatty acids). Serotonin (5-hydroxytryptamine (5-HT) is derived from tryptophan and functions as a neurotransmitter in the CNS and in the peripheral nervous system. More than 90% of 5-HT in the body is synthesized in the enterochromaffin cells in the gastrointestinal tract, where it regulates diverse gastrointestinal functions such as motility and secretory reflexes. The remainder is synthesized in the CNS in the raphe nuclei located in the brainstem, the ascending projections of which are involved in regulation of mood, appetite, memory, learning and sleep. SCFAs may also have a role to play in the synthesis and release of 5-HT from enterochromaffin cells. Dietary intervention studies also have reported an indirect mediational role for SCFAs in cognition and emotion.

Role of Inflammation: Growing evidence supports the role of increased inflammation in psychiatric disorders. C-reactive protein (CRP) has also been reported to be elevated in OCD patients. CRP has also been reported to have moderate-to-strong associations with some other psychiatric disorders. Caldirola et al (Ref 10) have shown that eCRP (elevated CRP) may be a transdiagnostic indicator of proinflammatory status in a considerable portion of patients with psychiatric disorders, including OCD. Hence there is documented association of increased CRP levels with greater illness severity, psychotropic treatment resistance, and increased cardiovascular risk.

The exact pathophysiological mechanisms for effectiveness of different types of OCD treatments are not understood in much detail. Some of the factors that are being researched as probable causes of OCD are dysfunctions on the hypothalamic-pituitary axis, neurotransmitters, vagus nerve, short-chain fatty acid metabolites, tryptophan, inflammatory factors and the brain-gut-microbiota axis. Many studies have shown that the intestine also has an effect on the central nervous system through vagal stimulation, intestinal permeability and the release of inflammatory and anti-inflammatory compounds and changes in circulating agents in the blood. Many studies have also focused on the leaky gut syndrome contributing to neuropathological disorders.

The main role of the intestinal barrier is in the digestion and absorption of nutrients: but it also controls the transport of antigens from the intestinal lumen into the submucosa, and maintains the balance between tolerance and the immune response to antigens that causes inflammation. The integrity of the intestinal barrier can be affected by diet, dysbiosis of the intestinal microbiota or by other factors. These have the potential to cause immune activation by translocation of microbial antigens and metabolites. (Ref 11, Iordache et al). Also, stress and anxiety can lead to a significant decrease in the villi/crypt ratio and the number of goblet cells.

Increased cortisol levels have been noted in patients with OCD. The altered levels of cortisol and immunological parameters are intimately linked with leaky gut and gut dysbiosis. The compromised gut integrity and activation of inflammatory processes have been linked to the pathophysiology of OCD. Moreover, the hyperactivation of the hypothalamic-pituitary-adrenal (HPA) axis has been correlated with gut dysbiosis (Ref 12 Ghuge et al).

The gut-brain axis refers to the bidirectional signalling mechanisms between the gastrointestinal tract and the central nervous system (CNS). Through complex neuro humoral pathways, signals from the brain can alter the sensorimotor and secretory functions of the gut, and conversely, visceral afferent signals originating in the gastrointestinal tract can modulate brain function. The gut microbiota is the ecological community of symbiotic and pathogenic microorganisms present in the gut, some of which can be critically involved in gut-brain communication. Imbalances in the microbial composition of the gut are present in gastrointestinal disorders such as IBS and coeliac disease, and metabolic disorders such as obesity and diabetes, as well as in mental illnesses such as eating disorders, autism spectrum disorder (ASD) and mood and anxiety disorders.

Microbiota-gut-brain (MGB) communication can theoretically occur through multiple systems comprising the gut-brain axis (including the autonomic nervous system and enteric nervous system), neuroendocrine systems and the immune system. Nevertheless, the specific mechanisms of this communication and its putative effects on human brain development, behaviour, cognition and mood are largely unknown.

OCD Diagnosis: OCD can be diagnosed only by a comprehensive evidence-based approach in both clinical and research practice. Obsessive-compulsive symptoms can be difficult to assess, given that they are often manifested internally, and individuals with OCD may not be inclined to recognize and report symptoms (ie, limited insight). DSM-IV (Ref 14, Diagnostic and Statistical Manual of Mental Disorders) gives several criteria for diagnosing OCD.

Hence, there is a lot of evidence indicating the role of the microbiome-gut-brain axis and compromised intestinal integrity in the pathophysiology of neuropsychological disorders. The current invention discloses the role of a multistrain probiotic formulation in OCD management, such as alleviating OCD symptoms, OCD prevention and treatment.

Embodiments

One embodiment of the current invention is a method of treating, preventing or ameliorating at least one symptom of obsessive-compulsive disorder (OCD) in a subject, the method comprising the step of administering to the subject a multistrain probiotic formulation comprising the bacterial strains *Bacillus coagulans, Lactobacillus rhamnosus, Bifidobacterium lactis, Lactobacillus plantarum, Bifidobacterium breve* and *Bifidobacterium infantis*.

In one embodiment, the multistrain probiotic formulation comprises the bacterial strains *Bacillus coagulans* Unique IS-2 (MTCC 5260), *Lactobacillus rhamnosus* UBLR-58 (MTCC 5402), *Bifidobacterium lactis* UBBLa-70 (MTCC 5400), *Lactobacillus plantarum* UBLP-40 (MTCC 5380), *Bifidobacterium breve* UBBr-01 (MTCC 25081) and *Bifidobacterium infantis* UBBI-01 (MTCC 25124).

In one embodiment, the multistrain probiotic formulation further comprises 100-500 mg of Glutamine. In one embodiment, the multistrain probiotic formulation comprises 250 mg of Glutamine.

In one embodiment, the method as disclosed herein, wherein the multistrain probiotic formulation comprises *Bacillus coagulans:Lactobacillus rhamnosus:Bifidobacterium lactis:Lactobacillus plantarum:Bifidobacterium breve* and *Bifidobacterium infantis* in the ratio 2:2:2:2:1:1. In one embodiment, the bacterial strains are present in the multistrain probiotic formulation at $10^6$-$10^{12}$ colony forming unit (cfu) per dose.

In one embodiment, the method as disclosed herein, wherein 1 to 2 doses of the multistrain probiotic formulation are administered to the subject per day. In one embodiment, the multistrain probiotic formulation is administered to the subject for at least 6 weeks. In one embodiment, the multistrain probiotic formulation is administered to the subject for 6-8 weeks.

In one embodiment, the multistrain probiotic formulation is administered to the subject as an adjunct to standard OCD treatment.

In one embodiment, the multistrain probiotic formulation is administered to the subject as part of a composition in the form of a food product, a dietary supplement or a pharmaceutically acceptable composition.

In one embodiment, the method disclosed herein, wherein the amelioration of OCD symptoms in the subject comprises a reduced level of repetitive behavior in the subject.

In one embodiment, administration of an effective dosage regimen of the multi-strain probiotic formulation disclosed herein reverses the elevated mRNA expression levels of IL-6, TNF-α and C-reactive associated with OCD in the subject.

In one embodiment, the method as disclosed herein, wherein the multistrain probiotic formulation produces Gamma-aminobutyric acid (GABA) from glutamine in the subject. In one embodiment, the administration of an effective dosage regimen of the multistrain probiotic formulation leads to increase in levels of GABA in the subject. In one embodiment, the administration of an effective dosage regimen of the multistrain probiotic formulation leads to decrease in levels of nNOS in the subject.

In one embodiment, the effective dose regimen of the multistrain probiotic formulation is administration of $10^6$ colony forming units to $10^{12}$ colony forming units (CFU) per dose of said formulation, for 6-8 weeks, administered at 1-2 doses per day. The amount of glutamine in the multi-strain probiotic formulation used herein for treating, preventing or improving the symptoms of OCD, is 100 mg to 500 mg, preferably 200 mg to 300 mg per single dose of the formulation.

In one embodiment, the effective dose regimen of the multistrain probiotic formulation is administration of $10^8$ colony forming units to $10^{10}$ colony forming units per dosage of said formulation, for 6-8 weeks, administered at 1-2 doses per day.

The effective amount of probiotic *Bacillus coagulans* Unique IS-2, *Lactobacillus rhamnosus* UBLR-58, *Bifidobacterium lactis* UBBLa-70, *Lactobacillus plantarum* UBLP-40, *Bifidobacterium breve* UBBr-01 and *Bifidobacterium infantis* UBBI-01 is $10^6$ colony forming units to $10^{12}$ colony forming units (CFU) per dosage of said formulation, but preferably $10^8$ colony forming units to $10^{10}$ colony forming units per dosage/dose of said formulation.

The bacterial strains in the formulation disclosed herein are in form of viable spores or in form of vegetative cells. The microbes are capable of germination and growth in the gut of the individual.

Glutamine is the precursor to the formation of GABA in the brain. Also, the multistrain probiotic formulation disclosed herein metabolizes the glutamine to produce the inhibitory neurotransmitter is GABA. The GABA-producing bacteria can produce GABA in the subject's gut. The GABA can diffuse into other systems of the subject's body (e.g., the circulatory and nervous systems). Therefore, the endogenous GABA can act as a neurotransmitter. In some embodiments, increased levels of GABA (e.g., in the nervous system) help to alleviate the symptoms of OCD.

In one embodiment, the multistrain probiotic formulation disclosed herein comprises probiotic strains that can produce GABA from Glutamine in a synergistic manner.

The multistrain probiotic formulation described in the invention is introduced into the gut of an individual by oral route in form of tablets, capsules, powders, gummies or liquids. The microbes are resistant to the environment of the stomach and the small intestine, and hence can move through this environment and lodge themselves in the gut of the individual.

In one embodiment, the effective dose of the probiotic formulation alleviates OCD symptoms, when compared to placebo control.

In one embodiment, method of treating OCD symptoms by the probiotic formulation disclosed herein, encompasses the restructuring of microbiome gut-brain axis. In one embodiment, this method encompasses treating gut dysbiosis in subjects or patients affected by OCD by the multistrain probiotic formulation disclosed herein, which helps in increasing gut eubiosis.

In one embodiment, the probiotic formulation used for treating OCD further comprises, or has added to: at least one probiotic or prebiotic, wherein optionally the prebiotic comprises an inulin, Fructooligosaccharides (FOS), Galactooligosaccharides (GOS), lactulose, extracts of artichoke, chicory root, oats, barley, various legumes, garlic, kale, beans or flacks or an herb.

In one embodiment, the probiotic formulation disclosed herein, further comprises an additive, examples of which include, but are not limited to, saline, a media, a defoaming agent, a surfactant agent, a lubricant, an acid neutralizer, a marker, a cell marker, a drug, an antibiotic, a contrast agent, a dispersal agent, a buffer or a buffering agent, a sweetening agent, a debittering agent, a flavouring agent, a pH stabilizer, an acidifying agent, a preservative, a desweetening agent and/or colouring agent, vitamin, mineral and/or dietary supplement, or a prebiotic nutrient.

In one embodiment, the probiotic formulation is administered in combination with other therapeutic or ameliorative agents for treating the symptoms of OCD. The currently known pharmacological interventions for treating OCD are well known to a person of skill in the art, and are also described herein to some extent.

In one embodiment, administration of the multi-strain probiotic formulation disclosed herein alleviates symptoms of OCD such as repetitive, compulsive, self-directed, and anxiety-like behavioural patterns.

In one embodiment, administration of the multi-strain probiotic formulation disclosed herein reverses the elevated mRNA expression levels of IL-6, TNF-$\alpha$ and C-reactive protein usually associated with OCD in patients.

In one embodiment, administration of the multi-strain probiotic formulation disclosed herein leads to increase in the number of goblet cells and improved crypt-to-villi ratio in the colon following probiotic treatment.

In one embodiment, the disrupted villi-to-crypt length ratio and goblet cells are restored to normal following multistrain probiotic treatment. The villi-to-crypt ratio of the intestine in humans gets perturbed due to the atrophy of villi in certain pathological conditions. In one embodiment, administration of the multi-strain probiotic formulation disclosed herein reverses the elevated levels of nNOS in the brains of OCD affected subjects. In one embodiment, that the reversal of OCD-like behavioural patterns with the treatment of selective multi-strain probiotics is mediated by remodelling of the gut-brain axis.

In one embodiment, treatment with multi-strain probiotic formulation disclosed herein restores the villi/crypt ratio restored to normal level after treatment. In one embodiment, treatment with multi-strain probiotic formulation positively impacts the intestinal epithelium and integrity.

In one embodiment, the administration of multistrain probiotic formulation effectively prevents the dysregulated abundance of Bacteroidetes and Firmicutes phyla, as well as the disrupted Firmicutes-to-Bacteroidetes (F/B) ratio found in dysbiotic guts, that may be associated with OCD.

The Firmicutes phylum, consisting of gram-positive bacteria, is recognized for its role in regulating the production of SCFAs, which have been associated with protection against OCD. Moreover, the decreased abundance of SCFAs-producing bacteria such as *Faecali bacterium prausnitzii, Roseburia,* and *Bacteroides* has been reported in neurological disorders.

EXAMPLES

Example 1: Multistrain Probiotic Formulation Preparation and GABA Producing Activity Testing of different ratios and combinations of the different strains was done to find out the optimal combination with the highest synergistic effect for producing GABA. The data and methodology are given below.

Microbial Strains:

A deposit of the six microbial strains of the multistrain probiotic formulation has been made in a depository affording permanence of the deposit and ready accessibility thereto by the public if a patent is granted. The strains with their corresponding accession numbers are given below:

i *Bacillus coagulans* Unique IS-2: MTCC-5260 ii *Lactobacillus rhamnosus* UBLR-58: MTCC 5402 iii *Bifidobacterium lactis* UBBLa-70: MTCC 5400 iv *Lactobacillus plantarum* UBLP-40: MTCC 5380 v *Bifidobacterium breve* UBBr-01: MTCC 25081 vi *Bifidobacterium infantis* UBBI-01: MTCC 25124

The Microbial Type Culture Collection and Gene Bank (MTCC facility in IMTECH, Sector-39, Chandigarh, India-160036) (https://mtccindia.res.in/), is an affiliate member of the World Federation for Culture Collections (WFCC) and is registered with the World Data Centre for Microorganisms (WDCM).

The experiment given below was done to test various combinations of the six different probiotic strains.

Methodology

Bacteria were inoculated in MRS broth containing 1% (w/v) mono sodium glutamate and incubated at 37° C. for 24 h. The culture was centrifuged at 10000×g for 10 min and 100 µL of supernatant was mixed with 400 µL of methanol and dried at 70° C. Approximately, 1 mL $LaCl_3$ (Lanthanum chloride) was added in to the tube, mixed thoroughly by vortexing and centrifuged at 10000×g for 5 min. The supernatant (700 µL) was collected and mixed with 160 µL of 0.1 M KOH. The mixture was then centrifuged and 200 µL of supernatant was diluted with potassium pyrophosphate buffer. From this, 550 µL of sample was measured for GABA. Each sample was added with 200 µL 0.5 M $K_4P_2O_7$, 150 µL 4 mM NADP, and 50 µL 2.0 units/mL Gabase (Sigma-Aldrich, USA). Initial absorbance was measured at 340 nm. Then 50 µL of 20 mM ketoglutaric acid was added and incubated at room temperature for 1 h. Final absorbance was measured at 340 nm to calculate the concentration.

Glutaminase Assay

Bacteria were cultivated and supernatant was obtained as described above. In brief, 500 µL of 0.04 M of L-glutamine prepared in 0.1 M phosphate buffer (pH 7.0) was mixed with 500 µL of supernatant and incubated at 37° C. for 30 min. Enzyme reaction was stopped by adding 500 µL of 1.5 M tri-chloro acetic acid. Then equal volume of Nessler's reagent (Potassium tetraiodomercurate-Potassium hydroxide solution: Sigma-Aldrich, USA) was added and incubated for 15 min or until appearance of yellow colour. Samples were centrifuged and absorbance of supernatant was measured at 450 nm. Ammonium sulphate was used as the standard. One IU of glutaminase was defined as the amount of enzyme that liberates one micromole of ammonia under optimum conditions.

Multistrain Probiotic Formulation GABA Producing Synergistic Activity:

It can be seen, as shown in Table 4, that the GABA producing activity of the four strains *Bifidobacterium infantis* UBBI-01, *Bifidobacterium breve* UBBr-01, *B. coagulans* Unique IS-2 and *B. lactis* UBBLa-70 (33.29, 25.85, 25.30 and 17.30 µM/ml respectively) is the highest amongst all the strains, and the other two strains *Lactobacillus plantarum* UBLP-40 and *Lactobacillus rhamnosus* UBLR-58a do not individually exhibit GABA producing activity. The combination of these four high GABA producing strains was tested (Table 4), and it was found, that unexpectedly, this combination of four high GABA producing strains does not show GABA producing activity equivalent to the combination of six strains (Table 1). The combination of these four strains which produce GABA individually at high levels, shows GABA producing activity of 33.18 µM/ml (Table 4), while when these four strains are combined together with the 2 other strains that individually do not show GABA producing activity, the resulting combination of the six strains shows GABA producing activity of 45.35 µM/ml (Table 1). Thus, it is clear that the two strains that do not individually show GABA producing activity, when present as a combination in the unique formulation disclosed in the current invention, increase the effect of the other four strains. Also, combinations of two and three strains shown in Tables 2 and 3, shows much lesser GABA producing activity of 29.73 and 18.78 µM/ml. Therefore, a synergistic effect is clearly evident in the unique combination of the six strains.

The ratio of the different strains was also finalised based on their GABA producing activity and subsequent experiments were done to validate the particular ratios. *Bifidobacterium breve* UBBR-01 and *Bifidobacterium infantis* UBB101 were found to produce the highest amounts of GABA and hence proportions of both these strains in the total strength of 10 billion colony forming units (cfu) was taken to be 1 billion cfu each, or in a ratio of 1:1. The remaining four strains were taken at 2 billion cfu each in the total strength of 10 billion cfu/capsule with a ratio of 2:2:2:2. Therefore, the ratio of the strains *L. plantarum* UBLP-40 (MTCC 5380):*L. rhamnosus* UBLR-58 (MTCC 5402):*B. coagulans* Unique IS-2 (MTCC 5260):*B. lactis* UBBLa-70 (MTCC 5400):*B. breve* UBBr-01 (MTCC 25081):*B. infantis* UBBI-01 (MTCC 25124) was decided to be optimal at 2:2:2:2:1:1 in the formulation.

TABLE 1

Individual glutaminase and GABA producing activities, and synergistic activity of the six strains combined together.

| Strains | Individual strains | |
| --- | --- | --- |
| | GABA µM/ml | Glutaminase IU/ml |
| *Lactobacillus plantarum* UBLP-40 | nil | 0.023 |
| *Lactobacillus rhamnosus* UBLR-58 | nil | 0.036 |
| *B. coagulans* Unique IS-2 | 25.30 | 0.051 |
| *Bifidobacterium infantis* UBBI-01 | 33.29 | 0.010 |
| *Bifidobacterium breve* UBBr-01 | 25.85 | 0.021 |
| *Bifidobacterium lactis* UBBLa-70 | 17.31 | 0.004 |
| Combination of 6 strains | 40.45 | 0.056 |

TABLE 2

Combination of two strains and synergistic activity of the two strain combination

| Combinations of two strains | GABA µM/ml | Glutaminase IU/ml |
| --- | --- | --- |
| *B. coagulans* Unique IS-2 *Bifidobacterium. infantis* UBBI-01 | 29.73 | 0.035 |

TABLE 3

| Combination of three strains and synergistic activity of the three strain combination | | |
| --- | --- | --- |
| Combinations of three strains | GABA μM/ml | Glutaminase IU/ml |
| *Lactobacillus plantarum* UBLP-40 *Lactobacillus rhamnosus* UBLR-58 *B. coagulans* Unique IS-2 | 18.78 | 0.023 |

TABLE 4

| Combination of 4 strains, and synergistic activity of the four strain combination | | |
| --- | --- | --- |
| Strains | GABA μM/ml | Glutaminase IU/ml |
| *B. coagulans* Unique IS-2 *Bifidobacteriuminfantis* UBBI-01 *Bifidobacterium breve* UBBr-01 *Bifidobacterium lactis* UBBLa-70 | 33.18 | 0.038 |

Thus, it is evident from the experiment and the data given above that different combinations of the strains were tested, and the combination of the six strains showed the maximum synergistic activity for the production of GABA & glutaminase activity. Hence this combination was selected for further studies. Therefore, the particular probiotic consortium disclosed in the current application, at the specific ratios disclosed, is capable of producing GABA at higher levels than the individual strains and also higher than the various other combinations of these strains comprising two, three or four strains.

Example 2: Behavioural Tests

Multistrain Probiotic Prevents Repetitive- and Compulsive-Like Behaviours in Marble-Burying, Self-Grooming, and Hole Board Test
Materials and Methods and Experimental Design
Animals Adult male Wistar rats (240±20 g) were purchased from Gentox Private Limited, Hyderabad. All experimental procedures were conducted in compliance with the guidelines set forth by the Committee for the Purpose of Control and Supervision of Experimentation on Animals (CPCSEA). The experimental design was approved by the Institutional Animal Ethics Committee (IAEC) of National Institute of Pharmaceutical Education and Research (NIPER) NIPER, Hyderabad (IAEC No. NIP/12/2021/PC/439). The animals were housed at standard temperature (22±2° C.), relative humidity (45-60%), and 12:12 h light:dark cycle with free access to a standard pellet diet and portable water ad libitum.

Figure 1A:
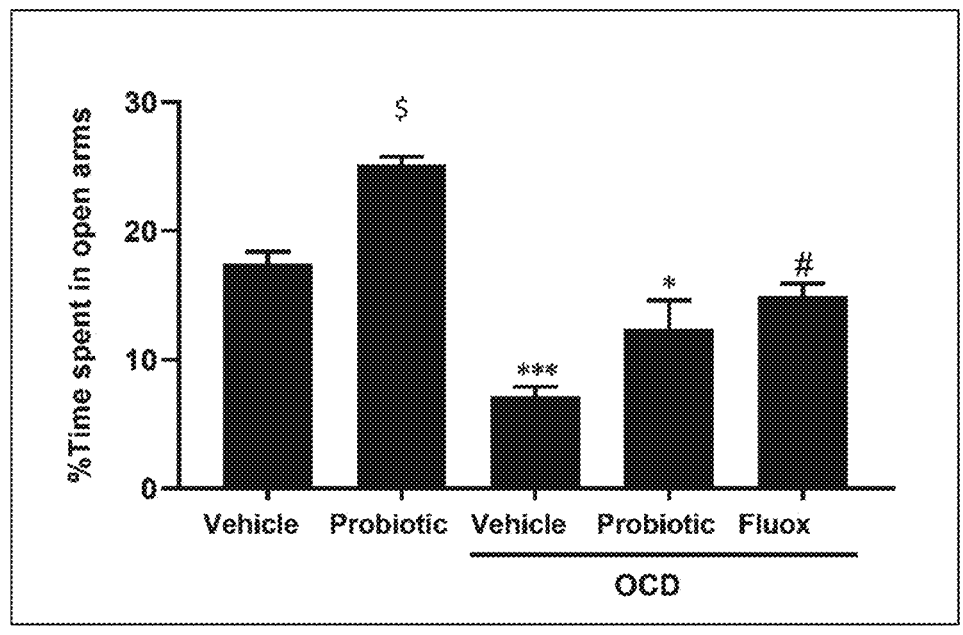
Figure 1B:
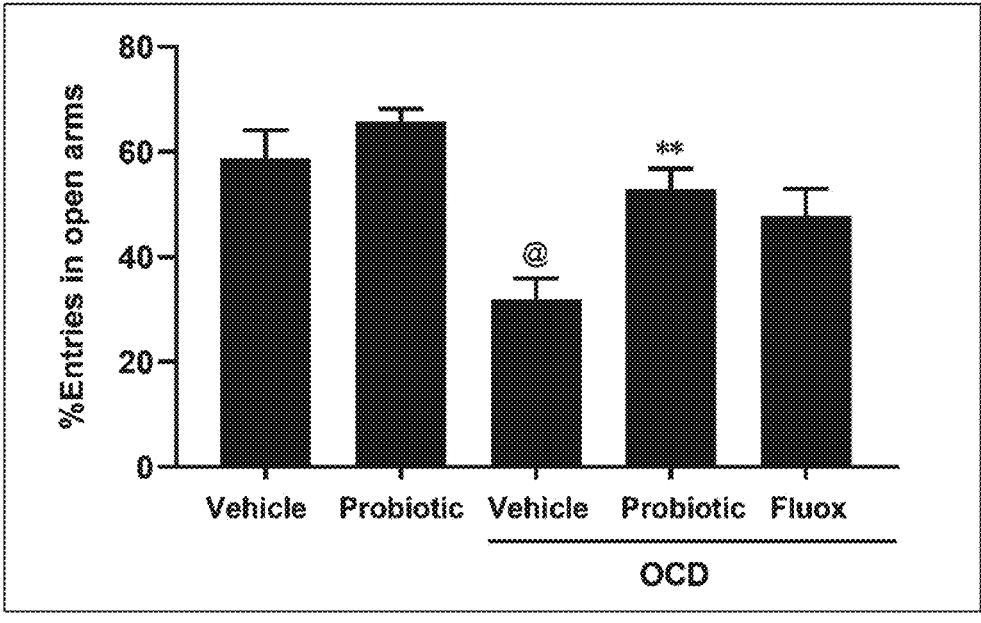

The multistrain probiotic capsules of 10 billion cfu containing *Bacillus coagulans* Unique IS-2. *Lactobacillus rhamnosus* UBLR-58, *Lactobacillus plantarum* UBLP-40, *Bifidobacterium lactis* UBBLa-70, *Bifidobacterium infantis* UBBI-01, and *Bifidobacterium breve* UBBr-01 with glutamine (250 mg), and relevant vehicle formulation (placebo without active ingredients) were used for further studies.
Experimental Design Experimental design was as given in Ref 12, incorporated herein in its entirety. The rats were randomly distributed into 5 different groups, with 6-8 rats per group (FIG. 1). Group 1, referred to as the "Vehicle" group, received the vehicle for a duration of 8 weeks. Group 2, denoted as the "Probiotic" group, received the peroral (PO) multistrain probiotic at a dose of 1× $10^{10}$ CFU per rat for 8 weeks. Group 3, labeled as the "Quinpirole" or "OCD" group, received a PO probiotic vehicle for 8 weeks and subcutaneous (SC) injections of quinpirole twice a week for 5 weeks at a dose of 0.5 mg/kg. Group 4, designated as the "Probiotic+Quinpirole" group, received the multistrain probiotic (1×$10^{10}$ CFU per rat, PO) for 8 weeks along with quinpirole (0.5 mg/kg, SC). Group 5, referred to as "Fluox+Quinpirole," was treated with fluoxetine (10 mg/kg, peroral) for 6 weeks in combination with quinpirole (0.5 mg/kg, SC).

Quinpirole ((−)-Quinpirole hydrochloride sc-253339 (Santa Cruz Biotechnology, Inc.) and fluoxetine (TCI Chemicals) were dissolved in normal saline and administered subcutaneously and via the PO route. Multistrain probiotic powder in the capsule was dissolved in water and administered via the PO route using rat oral gavage needles. At the end of 8 weeks of multistrain probiotic treatment, rats were subjected to different behavioral assays.

Fluoxetine is a type of antidepressant known as a selective serotonin reuptake inhibitor (SSRI). It's often used to treat depression, and sometimes obsessive-compulsive disorder and bulimia. It works by increasing the levels of serotonin in the brain. Serotonin is thought to have a good influence on mood, emotion and sleep.

Quinpirole is a psychoactive drug and research chemical which acts as a selective D2 and D3 receptor agonist. Quinpirole induces compulsive behaviour symptomatic of obsessive compulsive disorder in rats.
Statistical Analyses Statistical analyses were done using GraphPad Prism software. The data are presented as mean±standard error of the mean (Mean±S.E.M.) for each animal group. The behavioral, RT-PCR, and 16S rRNA gene sequencing data was processed employing one-way analysis of variance (ANOVA) and post-hoc Dunnett's and Tukey's multiple comparisons tests. Moreover, two-way ANOVA followed by post hoc Tukey's corrected (alpha) multiple comparisons test was employed to find the interaction between probiotics (active vs. vehicle) and quinpirole (active vs. vehicle) groups. Results are considered statistically significant when $p < 0.05$.

The above materials and methods, experimental design and statistical analysis was used for all the examples given herein.

Example 2.1. Multistrain Probiotic Prevents Anxiety-Like Effects in EPM

The increased exploration of open arms indicates an anxiolytic-like phenotype in rats. Quinpirole-injected rats (bars labelled as OCD) (0.5 mg/kg, twice weekly for 5 weeks) made fewer entries and spent less time in the open arms of EPM (elevated plus maze), depicting anxiety-like phenotypes (FIG. 1A, B). Administration of multistrain probiotic for 8 weeks significantly improved the time spent in open arms ($p < 0.039$) and entries in open arms ($p < 0.009$) compared to quinpirole. Application of 2-way ANOVA revealed a significant effect of treatment on % time spent in open arms [F (1, 24)=93.03, $p < 0.0001$] and % open arm entries [F (1, 25)=23.8, $p < 0.0001$]. Interestingly, the perse multistrain probiotic treatment showed a significant increase in time spent in open arms ($p < 0.0003$ vs. vehicle) without influencing the open arm entries ($p > 0.05$). Thus, no significant inter action of probiotic×quinpirole was noted [F (1, 24)=1.135, p=0.2974] and [F (1, 25)=2.943, p=0.0986] on % time spent in open arms and % open arm entries, respectively. Fluoxetine-recipient animals also showed improved open-arms activity.

Example 2.2 Marble Burying Test

A marble burying test was employed to assess the impulsive- and compulsive-like behavior (Ref 15, Schneider and Popik). The wood chip bedding was spread around 5 cm thick at the bottom of the polypropylene cage of 45×24×21 cm dimension. Then, nine transparent glass marbles (1.5 cm in diameter) were uniformly distributed in two lines. The individual rat was placed in the cage, and the number of marbles buried and covered was manually counted for a period of 10 min.

Figure 2A:
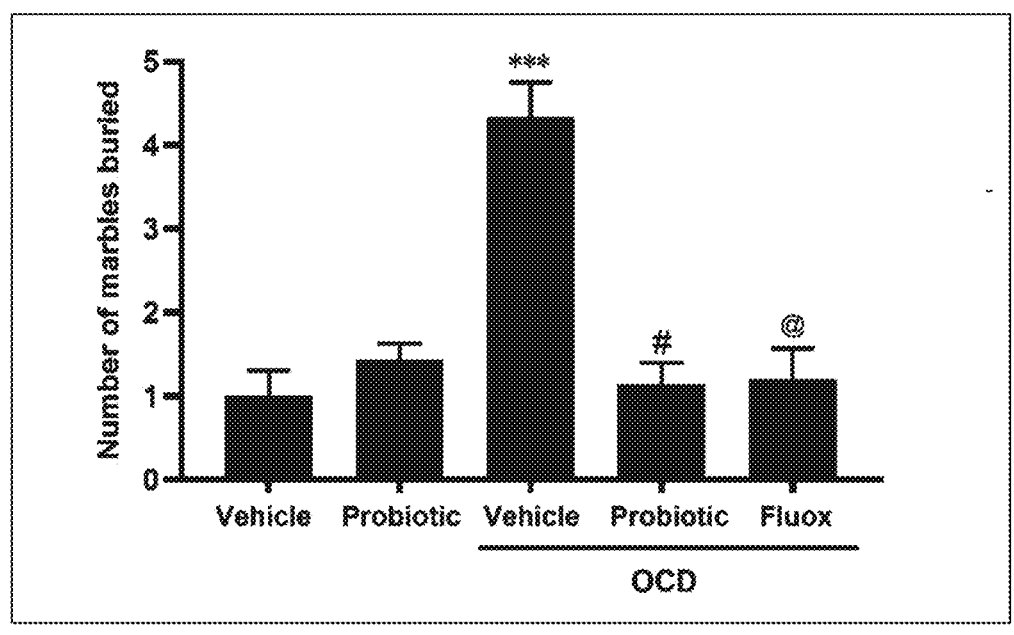

Repetitive and compulsive checking behaviors are the key hallmarks of OCD. We evaluated these phenotypes using the marble burying test. In comparison to the control group, in the quinpirole-injected rats considerably more marbles were buried (p<0.0001) (FIG. 2A). Quinpirole significantly increased the number of marbles buried among rats that received vehicle probiotic (p<0.0001), but not among those that received either probiotic or fluoxetine (both nonsignificant, FIG. 2A). Application two-way ANOVA followed by post-hoc Tukey's multiple comparisons test showed a significant interaction of probiotic×quinpirole [p<0.0001, df=1, F=36.40] in marble burring test. The results indicated the preventive responses of multistrain probiotics on the repetitive- and compulsive-like behaviors.

Example 2.2: Self-Grooming Test

The compulsion-like behavior was observed using a grooming test (Ref 16, Graf et al). The rats were placed for 10 min in a square-shaped transparent mouse cage without food and water for acclimatization. The grooming activities in the form of head shaking, vibration, genital grooming, face and head cleaning, body grooming, scratching, paw licking, and head shaking were observed for 10 min. The maximum score that could be achieved during the observation period was 40.

Figure 2B:
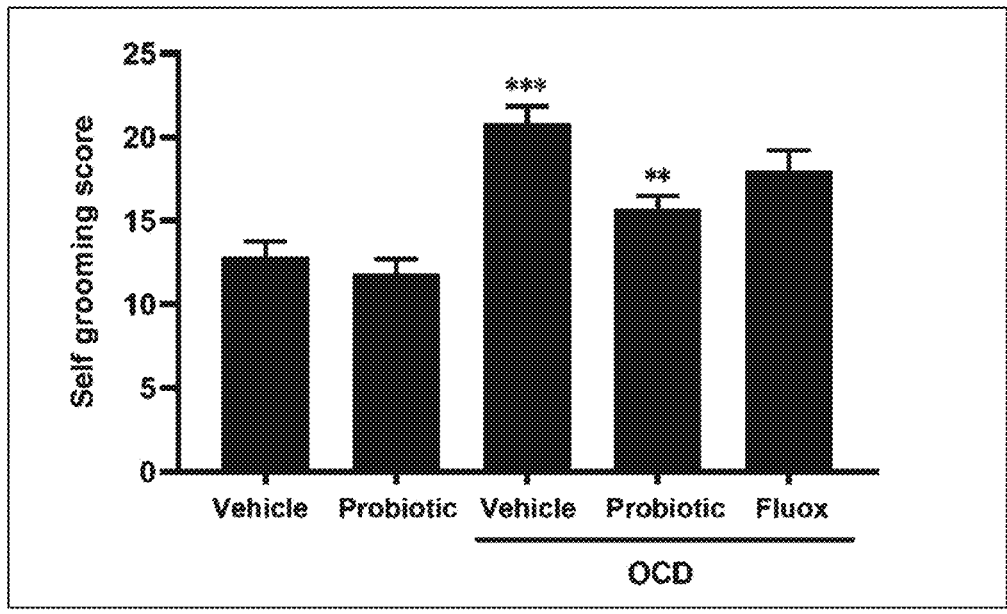

The repetitive, self-directed, and sequentially patterned behavior was assessed using a self-grooming test. Quinpirole-injected animals exhibited a higher grooming activity (p<0.0001) as compared to vehicle-treated animals. Eight weeks of multistrain probiotic treatment significantly reduced the number of grooming episodes (p<0.0014) compared to the quinpirole group (FIG. 2B). Application of 2-way ANOVA showed a significant interaction of probiotic× quinpirole [p=0.0243, df=1, F=5.67] in self-grooming activity. However, we did not notice any change in self-grooming score in fluoxetine-treated rats compared to the quinpirole group. The findings showed that the prophylactic use of the multistrain probiotic treatment had preventive effect on repetitive, self-directed, and sequentially patterned behavior associated with OCD.

Example 2.3: Hole Board Test

In this test, we measured the head-dipping behavior of rats, as described by Brown and Nemes (Ref 17). The total number of nose poking into the holes was automatically counted using ACTITRACK software (Panlab) during a 5-minute test session.

Figure 2C:
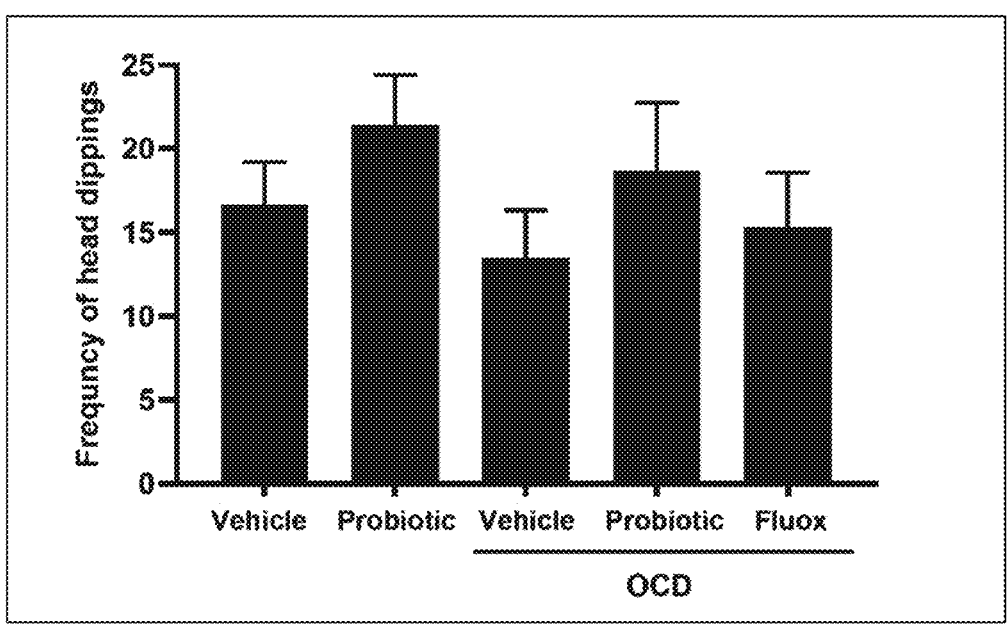

In the hole board test, quinpirole-injected rats showed a nonsignificant decrease (p>0.05) in head dipping activity compared to the vehicle group (FIG. 2C). Similarly, no interaction of probiotic× quinpirole [p=0.944, df=1, F=0.004] was noted in a two-way ANOVA analysis of head dipping data. The head dipping frequency was partially increased in multistrain probiotic treated animals, while less response was seen in fluoxetine-treated rats (p>0.05).

Example 2.4: Open Field Test (OFT)

The exploratory behavior of animals was evaluated using the open-field test (Ref 18, Ueno et al). Each rat was placed in the center of the box (50×50 cm), and allowed to freely explore for 10 min test duration. The ACTITRACK program automatically recorded the cage activity of animals.

Effect of Probiotic on Ambulatory Activity in OFT

Figure 3:
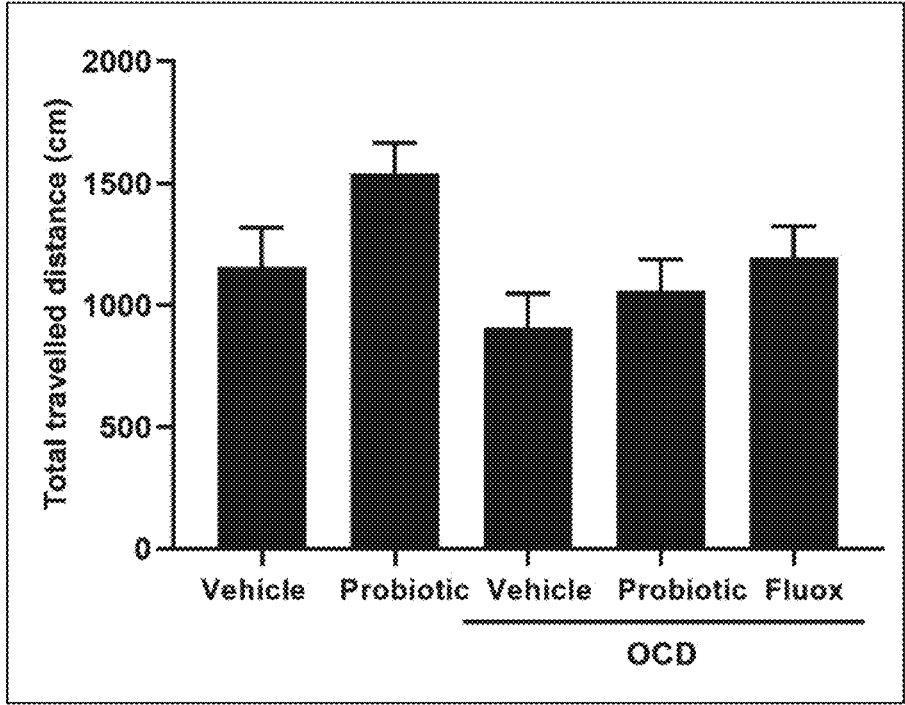

Gross locomotor activity was assessed using OFT. Data analysis using 2-way ANOVA revealed no appreciable differences (p>0.05) in the ambulatory activity of animals across the groups (FIG. 3). FIG. 3 shows a graph depicting the locomotor activity in OFT. Values are plotted as mean±S.E.M. for 6-8 rats. No bar is significantly different from the quinpirole group.

Example 3: Neurotransmitters Quantification in Frontal Cortex Using HPLC-ECD (Electrochemical Detection): Impact of Multistrain Probiotic on DA, NA, and 5-HT in the Frontal Cortex The concentrations of DA, NA, and 5-HT monoamines in the rat frontal cortex were measured using an earlier standardized protocol (Ref 19, Dandekar et al), and as described in Ref 12, incorporated herein in its entirety. Briefly, the samples were homogenized in one volume (2×) of diluents containing 0.2 M perchloric acid and 0.2 mg/mL L-cysteine and then centrifuged for 15 minutes at 14,000 rpm and 4° C. After that: the supernatants were collected to determine the concentration of monoamines such as dopamine, noradrenaline and 5-hydroxytryptamine (DA, NA, and 5-HT) using an HPLC-ECD equipment (BASi Epsilon ECD detector (PK/ 2008/006). The amounts of neurotransmitters were represented in ng/g tissue.

A nonsignificant decrease in the levels of 5-HT and NA and a slight increase in DA concentration was observed in the frontal cortex of quinpirole-injected rats as compared to perse multistrain probiotic-treated animals. However, no statistical difference (p>0.05) was noted across the treatment groups (Table 5).

TABLE 5

| Effect of multistrain probiotics on DA, NA, and 5-HT neurotransmitters in the frontal cortex | | | | |
|---|---|---|---|---|
| Neurotransmitters/ Groups | Perse Probiotic | Vehicle + Quinpirole | Probiotic + Quinpirole | Fluox + Quinpirole |
| NA (ng/g ± S.E.M.) | 230.08 ± 28.57 | 178.09 ± 8.05 | 236.85 ± 63.34 | 142.90 ± 46.99 |
| DA (ng/g ± S.E.M.) | 4.49 ± 2.36 | 15.83 ± 3.10 | 33.19 ± 13.38 | 9.60 ± 4.34 |
| 5-HT (ng/g ± S.E.M.) | 112.31 ± 22.67 | 58.73 ± 7.55 | 91.47 ± 22.74 | 53.25 ± 34.59 |

Example 4: Estimation of BDNF in the Frontal Cortex: Impact of Multistrain Probiotic on nNOS and BDNF in the Frontal Cortex BDNF was evaluated in frontal cortex brain samples using a commercial sandwich ELISA kit (#RAB1138-1KT).

Optical density was measured at 450 nm, and BDNF levels were expressed as mg/g of fresh tissue. Experiments were designed as described in Ref 20, Ghuge et al, incorporated herein in its entirety.

Radioimmunoprecipation Assay (RIPA) buffer was used to homogenize the frontal cortex part of the rat brain and then resolved using sodium dodecyl sulfate-polyacrylamide gel electrophoresis (SDS-PAGE). The proteins were then transferred to a nitrocellulose membrane, blocked with 5% bovine serum albumin, and incubated with the primary antibody anti-NOS1 (sc-5302, 1:1000 dilution) overnight at 4° C., followed by incubation with horseradish peroxidase-conjugate secondary antibody at RT. The required proteins were then detected by using an ECL solution.

Figure 4A:
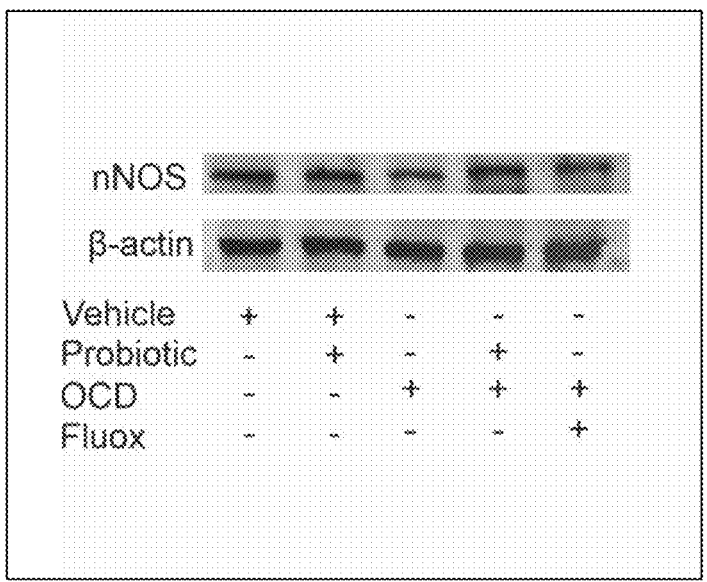
FIG. 4B shows a graph with nNOS levels in different groups. Values are plotted as mean±S.E.M. *p<0.0121 vs. vehicle: **p<0.0021 and #p<0.004 vs. quinpirole group.
Figure 4B:
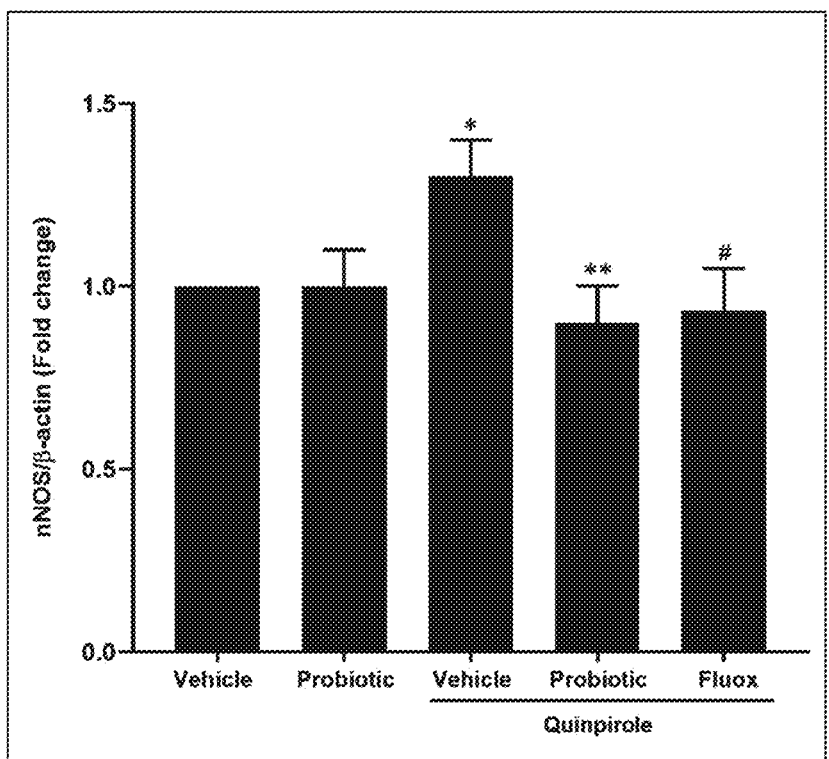
Figure 5:
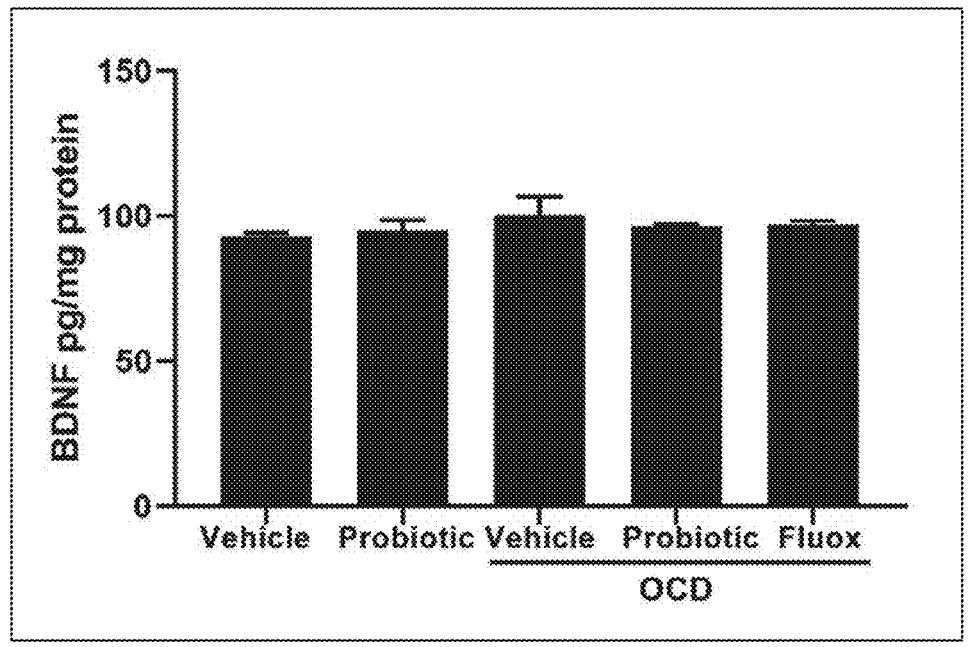
FIG. 5 shows a Graph depicting the detection of BDNF in the frontal cortex of rat brain. Values are plotted as mean±S.E.M.

We observed significantly increased levels of nNOS (p<0.0121) in the frontal cortex region of quinpirole-injected rats. Multistrain probiotic and fluoxetine treatment significantly reduced the expression of nNOS (p<0.0021 and p<0.004, respectively) compared to the quinpirole group (FIG. 4A, B). Application of 2-way ANOVA showed significant interaction of probiotic×quinpirole [p=0.0039, df=1, F=16] on nNOS expression. The BDNF levels in the frontal cortex of rats remained unaffected across the groups (FIG. 5)

Example 5: Cytokine Expression Analysis by Real-Time PCR Analysis: Multistrain Probiotic Dampens the Expression of Inflammatory Mediators in the Amygdala RT-PCR was performed to analyze the impact of a multistrain probiotic on cytokines mRNA expression (Ref 20, Rahman et al). Briefly, NucleoSpin® RNA isolation kit (#740955.50, DSS Takara Bio India Private Ltd) was used to extract RNA from the rat brain's amygdala. PrimeScript™ 1st strand cDNA synthesis kit (#6110A, DSS Takara Bio India Private Ltd) was used to process these RNA samples to cDNA. The 10 µL reaction mixture was prepared by mixing 5 µL of SYBR Green, 2 µL of the PCR primer (1 µL reverse+1 µL forward) (GCC Biotech, India, Private Ltd.). 1 µL of diluted cDNA template and 2 µL nuclease-free water. For each PCR test, the threshold cycle numbers were averaged across all samples. Using Δ/Δ Ct technique, the relative mRNA expression was calculated. The primers were designed (Table 6) using the software tools NCBI BLAST.

TABLE 6

Primer sequences used for the RT-PCR study of TNF-α, IL-6 and CRP

| Gene Name | Forward primer | Reverse primer |
|---|---|---|
| IL-6 | SEQ ID NO: 1 | SEQ ID NO: 2 |
| CRP | SEQ ID NO: 3 | SEQ ID NO: 4 |
| TNF-α | SEQ ID NO: 5 | SEQ ID NO: 6 |
| GAPDH | SEQ ID NO: 7 | SEQ ID NO: 8 |

We assessed the mRNA expression of TNF-α, IL-6, and CRP cytokines in the amygdala, a neuroanatomical framework known to be associated with the neuropathology of OCD (Refer 21, Meyer). A significant increase in IL-6 (p<0.0162) and CRP (p<0.0001) was noted in quinpirole-injected OCD rats. Multistrain probiotic treatment for 8 weeks significantly prevented the increased expression of IL-6 (p<0.0207) and CRP (p<0.0118) as compared to the quinpirole group (FIG. 6A-C). While increased levels of TNF-α (p=103) were noted in quinpirole rats, the effect was statistically insignificant. Two-way ANOVA applied for probiotic×quinpirole interaction showed [p=0.0277, p=0.0854 and p=0.0124, df=1 (for all), and F=6.62, F=3.43 and F=8.08] for TNF-α, IL-6 and CRP, respectively.

Example 6: Analysis for Short-Chain Fatty Acid (SCFAs): Effect of Multistrain Probiotic Therapy on SCFAs The gas chromatography-flame ionization detection (GC-FID) was used to evaluate the effect of OCD on bacterial metabolites as described earlier in our publications (Ref 22, Rahman et al & Ref 23, Satti et al). Briefly, supernatant acidified with HCL (5 M) and then extracted in diethyl ether to estimate the SCFAs. The acetate, propionate, and butyrate levels were estimated by loading the known amount of each SCFA.

As shown in Table 7, quinpirole-injected rats displayed lower levels of acetate, propionate, and butyrate as compared to the control group. Administration of multistrain probiotic and fluoxetine in quinpirole rats showed a nonsignificant increase in propionate (1.60±0.42 and 2.99±0.55) and butyrate (2.04±1.05 and 3.39±0.32) levels in fecal samples compared to OCD (3.39±0.32 and 1.70±0.73).

TABLE 7

Effect of multistrain probiotics on SCFAs levels in the fecal samples

| SN | Treatment | Acetate (µg/mL) (Mean ± S.E.M.) | Propionate (µg/mL) (Mean ± S.E.M.) | Butyrate (µg/mL) (Mean ± S.E.M.) |
|---|---|---|---|---|
| 1. | Vehicle | 1.90 ± 0.24 | 1.24 ± 0.23 | 1.16 ± 0.27 |
| 2. | Probiotic | 2.06 ± 0.24 | 2.10 ± 0.30 | 2.64 ± 0.49 |
| 3. | Vehicle + Quinpirole | 1.94 ± 0.14 | 1.25 ± 0.29 | 1.70 ± 0.73 |
| 4. | Probiotic + Quinpirole | 1.80 ± 0.30 | 1.60 ± 0.42 | 2.04 ± 1.05 |
| 5. | Fluox + Quinpirole | 2.51 ± 0.44 | 2.99 ± 0.55 | 3.39 ± 0.32 |

Example 7: Multistrain Probiotic Improves Colon Integrity

Histopathological Examination

To examine the gut permeability, H&E and alcian-blue PAS staining were performed. The method is already described in our publications (Ref 20, 21, and 22), incorporated herein in its entirety. Briefly, sections were processed for deparaffinization with xylene, rehydration with alcohol, and then stained with H&E and alcian blue-PAS agents. Finally, slides were mounted with (DPX) followed by observations under a microscope (Leica-ICC50 W).

In H&E (FIG. 7A) and Alican blue-PAS (FIG. 7A) staining of the colon, we observed a reduced number of mature goblet cells (p<0.0001) and villus height/crypt depth ratio (p<0.0394) in quinpirole rats compared to the control. Multistrain probiotic and fluoxetine treatment significantly increased the number of goblet cells (p<0.0001) and villus height/crypt depth ratio (p<0.0266) as compared to quinpirole-recipient rats (FIGS. 7C and 7D). Application of 2-way ANOVA also denoted a significant interaction of probiotic×quinpirole [p=0.008, df=1, F=10.55] and [p<0.0001, df=1, F=171.77], respectively. These findings indicate the improvement of gut permeability following preventive treatment of multistrain probiotic in rats (FIGS. 7A and 7B).

Example 8: Multistrain Probiotic Reforms the Intestinal Microbiota Diversity 16S rRNA Gene Sequencing for Intestinal Microbial Analysis The effect of OCD on microbial diversity was examined using 16S rRNA gene sequencing, as described earlier in Ref 20, incorporated herein in its entirety. Briefly, the fecal DNA was amplified at hypervariable V3 and V4 regions using forward RTPCR primer: GCCTACGGGNGGCWGCAG (SEQ ID NO: 9): reverse RTPCR primer: ACT-ACHVGGGTATCTAATCC (SEQ ID NO: 10) primers set. The amplicon libraries were quantified using a Qubit fluorometer after being purified with AMPureXP beads. According to the manufacturer's recommendations, the 4200 Tape Station system (Agilent Technologies) was used to examine the amplified libraries. The libraries were put (10-20 pM) onto the MiSeq for cluster creation and sequencing. Low-quality readings were trimmed using the FastQC trimmomatic v0.38 method to produce clean, high-quality reads. The high-quality clean reads were denoised and chimeric sequences were filtered through DABA2/Deblur.

The 16S rRNA gene amplicon results of faecal samples showed that administration of multistrain probiotic significantly impacted the Firmicutes (88.80%), Bacteroidetes (0.76%), Proteobacteria (0.23%), and Actinobacteria (3.30%) phylum phylum and community abundance of class (FIG. 8A) as compared to quinpirole group. We also observed a higher Firmicutes/Bacteroidetes (F/B) ratio in multistrain probiotic-treated rats compared to quinpirole group (FIG. 8B). The decreased relative abundance of *Lactobacillus* (FIG. 8B) and increased levels of *Allobaculum* (FIG. 8C), *Bifidobacterium* (FIG. 8D) and *Prevotella* genus in quinpirole rats were recovered after multistrain probiotic treatment. Furthermore, at the species level a reduced abundance of *Lactobacillus vaginalis* ($p<0.002$), *Lactobacillus reuteri* ($p<0.002$), and an increased relative abundance of *Bifidobacterium animalis* ($p<0.002$) and Ruminococcus flavefaciens was also reversed following multistrain probiotic administration in the quinpirole rats. The alpha diversity (eg. Chao1 index, Shannon index, and Simpson index) and the beta diversity of microbial communities remained unaffected across the treatment groups.

REFERENCES

1. Kantak, P. A., Bobrow, D. N., Nyby, J. G. (2014) Obsessive-compulsive-like behaviors in house mice are attenuated by a probiotic (*Lactobacillus rhamnosus* GG). Behav Pharmacol. 25(1):71-9.
2. Zheng, P., Zeng, B., Zhou, C., Liu, M., Fang, Z., Xu, X., Zeng, L., Chen, J., Fan, S., Du, X., Zhang, X., Yang, D., Yang, Y., Meng, H., Li, W., Melgiri, N. D., Licinio, J., Wei, H., Xie, P. (2016) Gut microbiome remodeling induces depressive-like behaviors through a pathway mediated by the host's metabolism. Mol Psychiatry. 21(6):786-96.
3. Jiang. H., Ling. Z., Zhang. Y., Mao. H., Ma, Z., Yin, Y., Wang. W., Tang. W., Tan, Z., Shi. J., Li. L . . . . Ruan. B. (2015) Altered fecal microbiota composition in patients with major depressive disorder. Brain Behav Immun. 48:186-94.
4. Sulthana. A., Lakshmi, S. G., Madempudi. R. S. (2019) High-quality draft genome and characterization of commercially potent probiotic *Lactobacillus* strains. Genomics Inform. 17(4): e43.
5. Kellner, M. (2010) Drug treatment of obsessive-compulsive disorder. Dialogues Clin Neurosci. 12(2):187-97.
6. Margoob, M. A., Chandel, R., Mushtaq, H., DhuhaMushtaq, D. (2014) Treatment-Resistant Obsessive-Compulsive Disorder (OCD) Current Understanding. In (Ed.), Obsessive-Compulsive Disorder—The Old and the New Problems. IntechOpen.
7. Hadi, F., Kashefinejad, S., Kamalzadeh, L., Hoobehfekr, S., Shalbafan, M. (2021) Glutamatergic medications as adjunctive therapy for moderate to severe obsessive-compulsive disorder in adults: a systematic review and meta-analysis. BMC Pharmacol Toxicol. 22(1):69.
8. Hertz, L. (2013) The Glutamate-Glutamine (GABA) Cycle: Importance of Late Postnatal Development and Potential Reciprocal Interactions between Biosynthesis and Degradation. Front Endocrinol (Lausanne). 4:59.
9. Biria, M., Banca, P., Healy, M. P. et al. (2023) Cortical glutamate and GABA are related to compulsive behaviour in individuals with obsessive compulsive disorder and healthy controls. Nat Commun 14, 3324.
10. Caldirola, D., Daccò, S., Cuniberti, F., Grassi, M., Lorusso, S., Diaferia, G., Perna, G. (2021) Elevated C-reactive protein levels across diagnoses: The first comparison among inpatients with major depressive disorder, bipolar disorder, or obsessive-compulsive disorder. J Psychosom Res. 150:110604.
11. Iordache, M. M., Tocia, C., Aschie, M., Dumitru, A., Manea, M., Cozaru, G. C., Petcu, L., Vlad, S. E., Dumitru, E., Chisoi, A. (2022) Intestinal Permeability and Depression in Patients with Inflammatory Bowel Disease. J Clin Med. 11(17):5121.
12. Ghuge, S., Rahman, Z., Bhale, N. A., Dikundwar, A. G., Dandekar, M. P. (2023) Multistrain probiotic rescinds quinpirole-induced obsessive-compulsive disorder phenotypes by reshaping of microbiota gut-brain axis in rats. Pharmacol Biochem Behav. 232:173652.
13. Turna, J., Grosman Kaplan, K., Anglin, R., Patterson, B., Soreni, N., Bercik, P., Surette, M. G., Van Ameringen, M. (2020) The gut microbiome and inflammation in obsessive-compulsive disorder patients compared to age- and sex-matched controls: a pilot study. Acta Psychiatr Scand. 142(4):337-347.
14. Diagnostic and Statistical Manual of Mental Disorders, 5th Edition: DSM-5 (American Psychiatric Association)
15. Schneider, T., Popik, P. (2007) Attenuation of estrous cycle-dependent marble burying in female rats by acute treatment with progesterone and antidepressants. Psychoneuroendocrinology. 32(6):651-9.
16. Graf, M., Kantor, S., Anheuer, Z. E., Modos, E. A., Bagdy, G. (2003) m-CPP-induced self-grooming is mediated by 5-HT2C receptors. Behav Brain Res 142(1-2): 175-9.
17. Brown, G. R., Nemes, C. (2008) The exploratory behaviour of rats in the hole-board apparatus: is head-dipping a valid measure of neophilia? Behav Processes. 78(3):442-8.
18. Ueno, H., Takahashi, Y., Suemitsu, S. et al. (2020) Effects of repetitive gentle handling of male C57BL/6NCrl mice on comparative behavioural test results. Sci Rep 10, 3509.
19. Dandekar, M. P., Diaz, A. P., Rahman, Z., Silva, R. H., Nahas, Z., Aaronson, S., Selvaraj, S., Fenoy, A. J., Sanches, M., Soares, J. C., Riva-Posse, P., Quevedo, J. (2022) A narrative review on invasive brain stimulation for treatment-resistant depression. Braz J Psychiatry. 44(3):317-330.

20. Rahman, Z., Bhale, N. A., Dikundwar, A. G., Dandekar, M. P. (2023) Multistrain Probiotics with Fructooligosaccharides Improve Middle Cerebral Artery Occlusion-Driven Neurological Deficits by Revamping Microbiota-Gut-Brain Axis. Probiotics Antimicrob Proteins.

21. Meyer, J. (2021) Inflammation, Obsessive-Compulsive Disorder, and Related Disorders. Curr Top Behav Neurosci. 49:31-53.

22. Rahman, A., Alqaisi, S., Nath, J. (2023) A Case of *Lactobacillus* casei Endocarditis Associated With Probiotic Intake in an Immunocompromised Patient. Cureus. 15(4):e38049.

23. Satti, S., Palepu, M. S. K., Singh, A. A., Jaiswal, Y., Dash, S. P., Gajula, S. N. R., Chaganti, S., Samanthula, G., Sonti, R., Dandekar, M. P. (2023) Anxiolytic- and antidepressant-like effects of *Bacillus coagulans* Unique IS-2 mediate via reshaping of microbiome gut-brain axis in rats. Neurochem Int. 163:105483.

---

We claim:

1. A method of treating, preventing or ameliorating at least one symptom of obsessive compulsive disorder (OCD) in a subject, the method comprising the step of administering to the subject a multistrain probiotic formulation comprising the bacterial strains *Bacillus coagulans, Lactobacillus rhamnosus, Bifidobacterium lactis, Lactobacillus plantarum, Bifidobacterium breve* and *Bifidobacterium infantis* and Glutamine in a concentration range of 100-500 mg.

2. The method of claim 1, wherein the multistrain probiotic formulation comprises the bacterial strains *Bacillus coagulans* Unique IS-2 deposited under accession number MTCC 5260, *Lactobacillus rhamnosus* UBLR-58 deposited under accession number MTCC 5402, *Bifidobacterium lactis* UBBLa-70 deposited under accession number MTCC 5400, *Lactobacillus plantarum* UBLP-40 deposited under accession number MTCC 5380, *Bifidobacterium breve* UBBr-01 deposited under accession number MTCC 25081 and *Bifidobacterium infantis* UBBI-01 deposited under accession number MTCC 25124.

3. The method of claim 1, wherein the multistrain probiotic formulation comprises *Bacillus coagulans:Lactobacillus rhamnosus:Bifidobacterium lactis:Lactobacillus plantarum:Bifidobacterium breve* and *Bifidobacterium infantis* in the ratio 2:2:2:2:1:1.

4. The method of claim 1, wherein the bacterial strains are present in the multistrain probiotic formulation at $10^6$-$10^{12}$ colony forming unit (cfu) per dose.

5. The method of claim 1, wherein the multistrain probiotic formulation is administered to the subject 1 to 2 doses per day.

6. The method of claim 1, wherein the multistrain probiotic formulation is administered to the subject for at least 6 weeks.

7. The method of claim 1, wherein the multistrain probiotic formulation is administered to the subject for 6-8 weeks.

8. The method of claim 1, wherein the method comprises administering an effective dosage regimen of the multistrain probiotic formulation to the subject, wherein the effective dosage regimen comprises administering the multistrain probiotic formulation 1 to 2 doses per day for 6-8 weeks.

9. The method of claim 1, wherein the multistrain probiotic formulation is administered to the subject as an adjunct to standard OCD treatment.

10. The method of claim 1, wherein the multistrain probiotic formulation is administered to the subject in the form of a food product, a dietary supplement or a pharmaceutically acceptable composition.

11. The method of claim 1, wherein the amelioration of the OCD symptom is a reduced level of repetitive behavior in the subject.

12. The method of claim 1, wherein the multistrain probiotic formulation produces Gamma-aminobutyric acid (GABA) from glutamine in the subject.

13. The method of claim 8, wherein the administration of the effective dosage regimen of the multistrain probiotic formulation to the subject increases Gamma-aminobutyric acid (GABA) levels in the subject.

14. The method of claim 8, wherein the administration of the effective dosage regimen of the multistrain probiotic formulation ameliorates or prevents OCD symptoms in the subject by increasing Gamma-aminobutyric acid (GABA) levels in the subject.

15. The method of claim 8, wherein the administration of the effective dosage regimen of the multistrain probiotic formulation leads to a decrease in levels of nNOS in the subject.

16. The method of claim 8, wherein the administration of the effective dosage regimen of the multistrain probiotic formulation to the subject leads to an increase in the number of goblet cells and improved crypt-to-villi ratio in the colon of the subject.

17. The method of claim 8, wherein the administration of the effective dosage regimen of the multi-strain probiotic formulation reverses the elevated mRNA expression levels of IL-6, TNF-α and C-reactive associated with OCD in the subject.

*     *     *     *     *

SEQUENCE LISTING

```
Sequence total quantity: 10
SEQ ID NO: 1            moltype = DNA  length = 19
FEATURE                 Location/Qualifiers
source                  1..19
                        mol_type = other DNA
                        organism = synthetic construct
SEQUENCE: 1
acttcacaag tcggaggct                                              19

SEQ ID NO: 2            moltype = DNA  length = 19
FEATURE                 Location/Qualifiers
source                  1..19
                        mol_type = other DNA
                        organism = synthetic construct
SEQUENCE: 2
gcacactagg tttgccgag                                              19

SEQ ID NO: 3            moltype = DNA  length = 22
FEATURE                 Location/Qualifiers
source                  1..22
                        mol_type = other DNA
                        organism = synthetic construct
SEQUENCE: 3
tcacgataag cttctctcag gc                                          22

SEQ ID NO: 4            moltype = DNA  length = 20
FEATURE                 Location/Qualifiers
source                  1..20
                        mol_type = other DNA
                        organism = synthetic construct
SEQUENCE: 4
cccgtcaagc caaagctcta                                             20

SEQ ID NO: 5            moltype = DNA  length = 20
FEATURE                 Location/Qualifiers
source                  1..20
                        mol_type = other DNA
                        organism = synthetic construct
SEQUENCE: 5
ggctttcgga actcactgga                                             20

SEQ ID NO: 6            moltype = DNA  length = 20
FEATURE                 Location/Qualifiers
source                  1..20
                        mol_type = other DNA
                        organism = synthetic construct
SEQUENCE: 6
cccgtagggc gattacagtc                                             20

SEQ ID NO: 7            moltype = DNA  length = 19
FEATURE                 Location/Qualifiers
source                  1..19
                        mol_type = other DNA
                        organism = synthetic construct
SEQUENCE: 7
gcaagagaga ggccctcag                                              19

SEQ ID NO: 8            moltype = DNA  length = 20
FEATURE                 Location/Qualifiers
source                  1..20
                        mol_type = other DNA
                        organism = synthetic construct
SEQUENCE: 8
tgtgagggag atgctcagtg                                             20
```

-continued

```
SEQ ID NO: 9         moltype = DNA   length = 18
FEATURE              Location/Qualifiers
source               1..18
                     mol_type = other DNA
                     organism = synthetic construct
SEQUENCE: 9
gcctacgggn ggcwgcag                                              18

SEQ ID NO: 10        moltype = DNA   length = 20
FEATURE              Location/Qualifiers
source               1..20
                     mol_type = other DNA
                     organism = synthetic construct
SEQUENCE: 10
actachvggg tatctaatcc                                            20
```